(12) United States Patent
Park

(10) Patent No.: US 10,143,533 B2
(45) Date of Patent: Dec. 4, 2018

(54) BLOOD VESSEL SIZING DEVICE

(71) Applicant: SIZER LLC, St. Charles, IL (US)

(72) Inventor: Richard B. Park, St. Charles, IL (US)

(73) Assignee: SIZER LLC, St. Charles, IL (US)

( * ) Notice: Subject to any disclaimer, the term of this patent is extended or adjusted under 35 U.S.C. 154(b) by 0 days.

(21) Appl. No.: 15/287,337

(22) Filed: Oct. 6, 2016

(65) Prior Publication Data

US 2018/0098820 A1    Apr. 12, 2018

(51) Int. Cl.
*G06K 9/00* (2006.01)
*A61B 90/00* (2016.01)
(Continued)

(52) U.S. Cl.
CPC .............. *A61B 90/39* (2016.02); *A61B 5/055* (2013.01); *A61B 5/1072* (2013.01); *A61B 5/1075* (2013.01); *A61B 5/1076* (2013.01); *A61B 5/1079* (2013.01); *A61B 6/12* (2013.01); *A61B 6/481* (2013.01); *A61B 6/504* (2013.01); *A61B 6/583* (2013.01); *G06T 5/50* (2013.01); *G06T 7/0012* (2013.01); *G06T 7/0022* (2013.01); *G06T 7/0042* (2013.01); *A61B 5/4887* (2013.01); *A61B 6/461* (2013.01); *A61B 2034/107* (2016.02); *A61B 2090/061* (2016.02); *A61B 2090/067* (2016.02); *A61B 2090/374* (2016.02); *A61B 2090/376* (2016.02); *A61B 2090/3937* (2016.02); *A61B 2090/3966* (2016.02); *A61B 2090/3991* (2016.02); *A61F 2/00* (2013.01); *A61F 2/95* (2013.01); *A61F 2250/0096* (2013.01); *G01B 15/00* (2013.01);
(Continued)

(58) Field of Classification Search
CPC .............. A61B 90/39; A61B 17/12109; A61B 17/12122; A61B 17/12172; A61B 17/221
USPC ............. 382/130; 604/518, 151, 500, 93.01; 128/898; 600/407, 481; 378/162, 165
See application file for complete search history.

(56) References Cited

U.S. PATENT DOCUMENTS

| 3,812,842 A | 5/1974 | Rodriguez |
| 4,061,924 A | 12/1977 | Jacoby et al. |

(Continued)

FOREIGN PATENT DOCUMENTS

| CN | 203436327 U | 2/2014 |
| JP | 2012081136 A | 4/2012 |
| WO | 2010064049 A1 | 6/2010 |

OTHER PUBLICATIONS

Jun. 14, 2013—(WO) International Search Report and Written Opinion—App. No. PCT/US2013/033154, dated Jun. 14, 2013—9 pages.
(Continued)

*Primary Examiner* — Charlotte M Baker
(74) *Attorney, Agent, or Firm* — Banner & Witcoff, Ltd.

(57) ABSTRACT

Medical devices and methods that provide for improved accuracy when positioning of a synthetic structure, such as a MEMS device or a stent, within a biological feature of a patient, such as a blood vessel, are disclosed. A blood vessel sizing device is configured for placement on the skin of a patient near a feature of interest (e.g. a blood vessel to be imaged). The device may include one or more radiopaque elements, including a target element, and one or more positioning markers having known sizes. A clinician may use the radiopaque elements to identify a portion of a blood vessel suitable for positioning of the synthetic structure.

20 Claims, 23 Drawing Sheets

(51) Int. Cl.
  *A61B 6/12* (2006.01)
  *A61B 6/00* (2006.01)
  *G06T 5/50* (2006.01)
  *G06T 7/00* (2017.01)
  *A61B 5/055* (2006.01)
  *A61B 5/107* (2006.01)
  *A61F 2/00* (2006.01)
  *A61F 2/95* (2013.01)
  *G01R 33/56* (2006.01)
  *A61B 34/10* (2016.01)
  *A61B 5/00* (2006.01)
  *G01B 15/00* (2006.01)
  *G01R 33/563* (2006.01)

(52) U.S. Cl.
  CPC ...... *G01R 33/5601* (2013.01); *G01R 33/5635* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/30101* (2013.01); *G06T 2211/404* (2013.01)

(56) References Cited

U.S. PATENT DOCUMENTS

| | | |
|---|---|---|
| 4,506,676 A | 3/1985 | Duska |
| 5,150,292 A | 9/1992 | Hoffmann et al. |
| 5,193,106 A | 3/1993 | DeSena |
| 5,216,700 A | 6/1993 | Cherian |
| 5,400,513 A | 3/1995 | Duffield |
| 5,970,119 A | 10/1999 | Hofmann |
| 6,084,941 A | 7/2000 | Stenstrom |
| 6,333,970 B1 | 12/2001 | LeMaitre et al. |
| 6,356,621 B1 | 3/2002 | Furumori et al. |
| 6,733,489 B2 | 5/2004 | Nutting et al. |
| 7,127,826 B2 | 10/2006 | Russell |
| 7,602,883 B2 * | 10/2009 | Joseph ............... A61B 5/6842 378/162 |
| 7,860,290 B2 | 12/2010 | Gulsun et al. |
| 7,876,884 B2 | 1/2011 | Davis |
| 7,978,825 B2 | 7/2011 | Ngo |
| 8,057,396 B2 | 11/2011 | Forster et al. |
| 8,298,147 B2 | 10/2012 | Huennekens et al. |
| 8,340,781 B2 * | 12/2012 | Konishi ............ A61B 5/02007 29/592.1 |
| 8,611,697 B2 | 12/2013 | Nathaniel et al. |
| 8,655,042 B2 | 2/2014 | Florent |
| 2004/0034298 A1 | 2/2004 | Johnson et al. |
| 2004/0086082 A1 | 5/2004 | Foos et al. |
| 2004/0133129 A1 | 7/2004 | Harari et al. |
| 2005/0000133 A1 | 1/2005 | Russell |
| 2007/0163139 A1 | 7/2007 | Russell |
| 2007/0213686 A1 * | 9/2007 | Mathur ............... A61M 5/1723 604/518 |
| 2007/0280406 A1 | 12/2007 | Geliebter |
| 2008/0187245 A1 | 8/2008 | Habets et al. |
| 2009/0022272 A1 | 1/2009 | Joseph et al. |
| 2009/0253981 A1 | 10/2009 | Hamilton et al. |
| 2012/0059244 A1 | 3/2012 | McClelland et al. |
| 2012/0302863 A1 | 11/2012 | O'Neill |
| 2013/0253301 A1 * | 9/2013 | Park ..................... A61B 5/1075 600/407 |
| 2014/0064582 A1 | 3/2014 | Schmidt et al. |
| 2014/0221874 A1 | 8/2014 | Park |
| 2017/0309016 A1 * | 10/2017 | Klaiman ............ A61B 6/4441 |

OTHER PUBLICATIONS

Feb. 4, 2016—(WO) Invitation to Pay Additional Fees and Partial Search Report—App. No. PCT/US2015/024925—6 pages.
Apr. 19, 2016—(WO) International Serch Report and Written Opinion—App. No. PCT/US2015/024925—17 pages.
Jan. 23, 2018—(WO) International Search Report and Written Opinion—App. No. PCT/US2017/055606—16 pages.

* cited by examiner

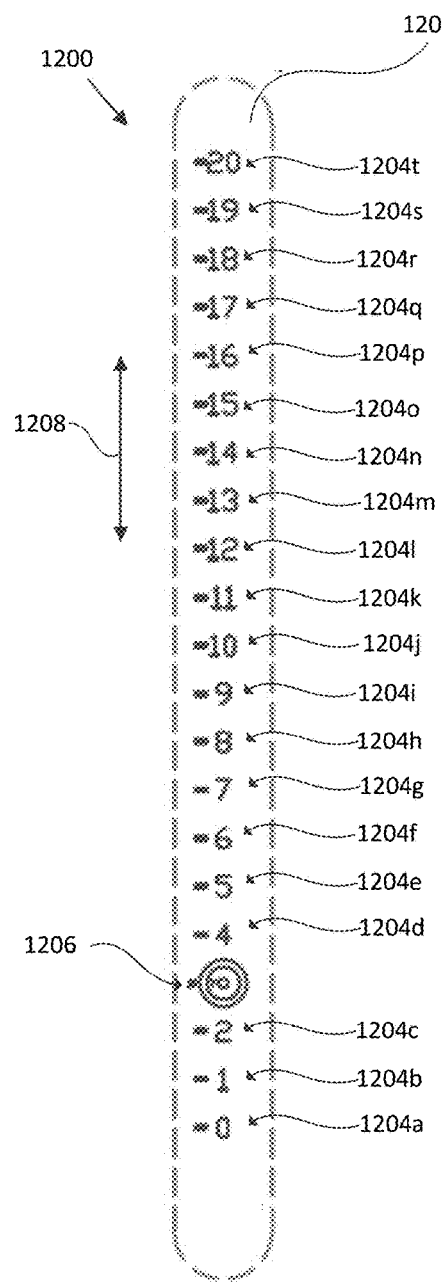
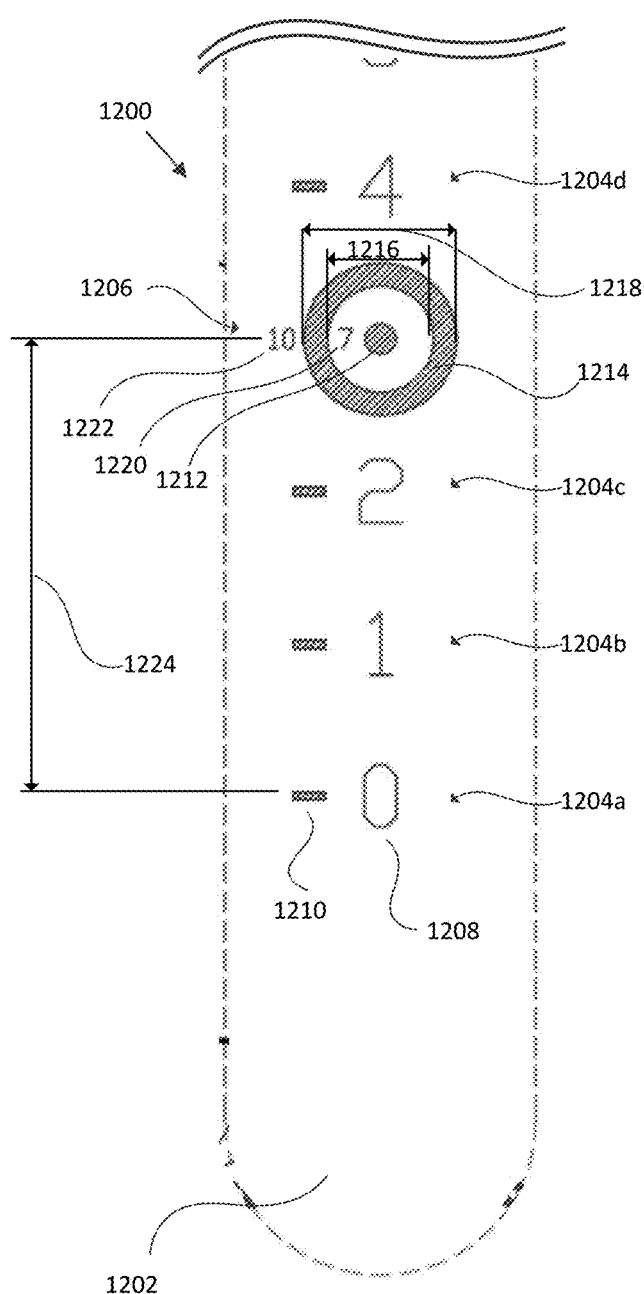
FIG. 12A
FIG. 12B

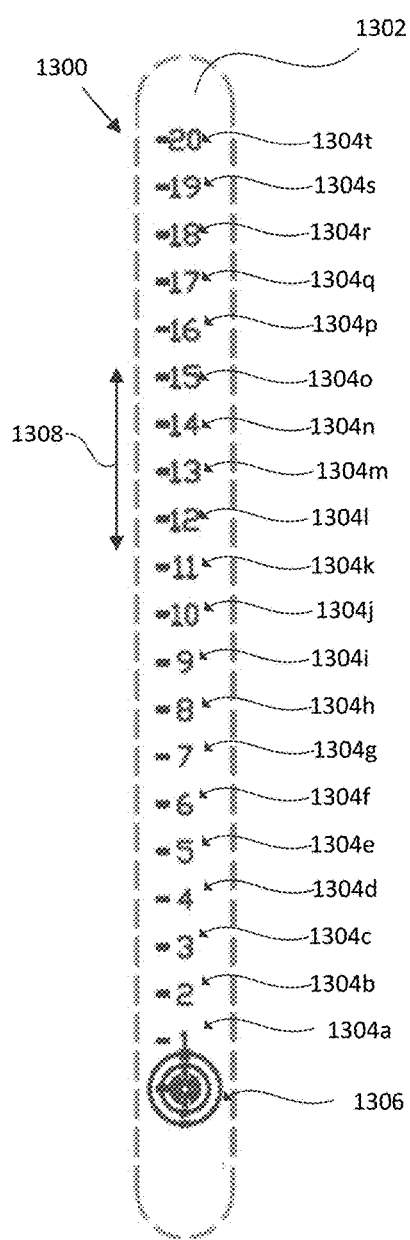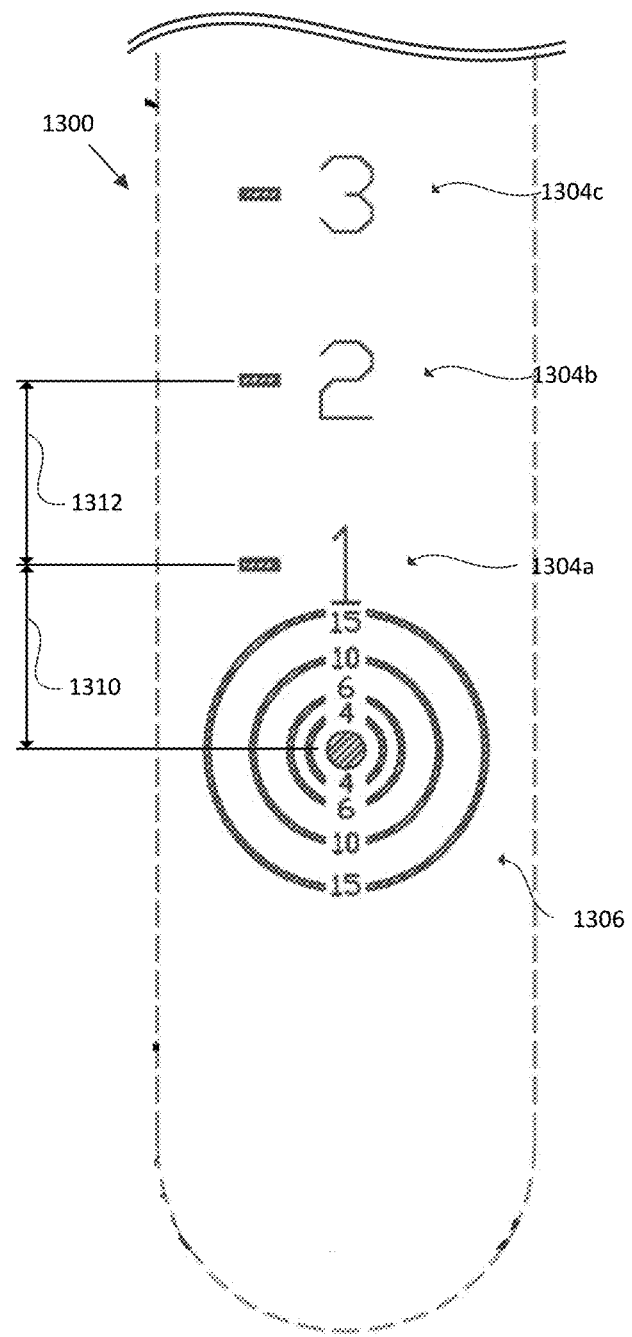
FIG. 13A
FIG. 13B

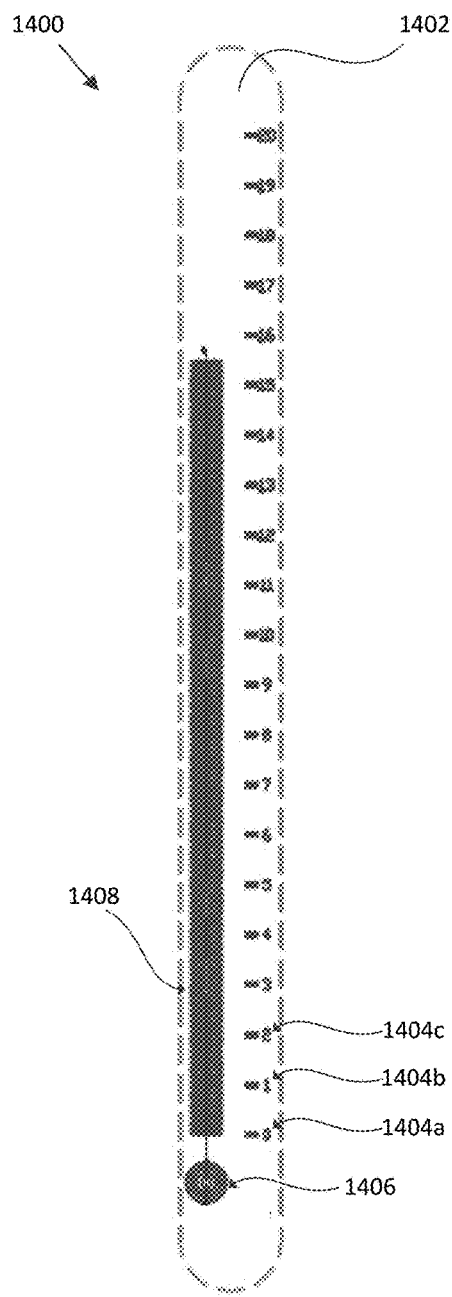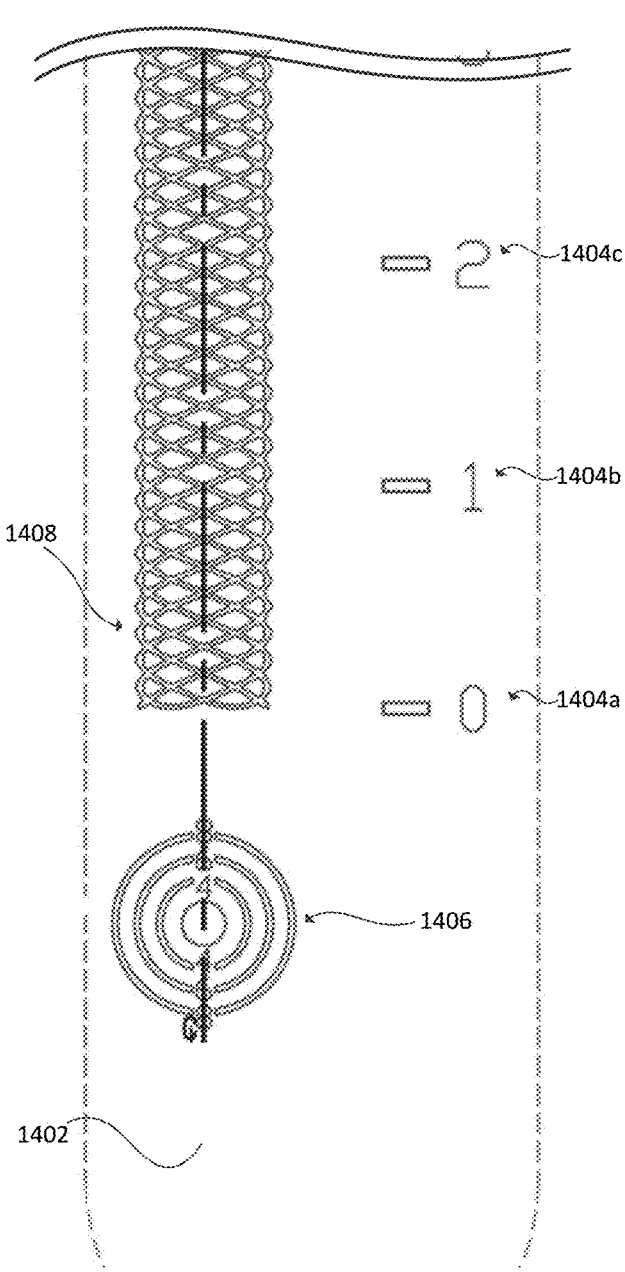
FIG. 14A
FIG. 14B

BLOOD VESSEL SIZING DEVICE

BACKGROUND

The present disclosure relates generally to medical devices, and more specifically, to systems and methods for determining dimensions of objects imaged within a radiological image, and for correct positioning of a synthetic structure within a biological feature of a patient.

Determining blood vessel size quickly and accurately is important, for example, for correct positioning of a MEMS device for monitoring of physiological parameters of a patient.

Diagnostic imaging using, for example, x-ray machines in combination with a contrast agent introduced into the blood stream of a patient, may generate images of one or more of the patient's blood vessels. However, the contrast agent may be associated with side effects if used in high quantities.

A need accordingly exists for medical devices and methods that improve the process of determining blood vessel size during and positioning of a MEMS device, while reducing the amount of contrast agent used.

SUMMARY

Aspects of the present disclosure relate to systems, devices, and methods that provide for improved accuracy when positioning of a synthetic structure, such as a MEMS device or a stent, within a biological feature, such as a blood vessel, of a patient. In one example, the present disclosure is directed to medical devices and methods that provide for more accurate measurement of biological features represented in a radiological image. In one implementation, a blood vessel sizing device is configured for placement on the skin of a patient near a feature of interest (e.g. a blood vessel to be imaged). Accordingly, the device may include one or more radiopaque elements, including a target element, and one or more positioning markers having known sizes. When a computer machine generates a radiological image of the blood vessel, the radiopaque elements cause the features of known size to be visible on the generated image (along with the blood vessel image). As such, a clinician may quickly and accurately determine the actual size (true dimension/length) of one or more portions of the blood vessel(s), and identify a portion of a blood vessel suitable for positioning of the synthetic structure.

In one aspect, a method and a non-transitory computer-readable medium comprising computer-executable instructions is described for positioning of a synthetic structure at a biological feature of a patient. The methods and instructions include receiving first radiological image data of an area of a body of a patient as a radiopaque contrast agent is present in one or more biological features within the area. Further, the instructions include identifying, within the received first radiological image data, a radiopaque target element of a sizing device positioned on an area of skin of the patient. The radiopaque target element is compared to one or more biological features to identify a selected biological feature with a dimensional property within an acceptable dimensional range, as indicated by the radiopaque target element. A target location of the selected biological feature relative to one or more radiopaque positioning markers of the sizing device is determined. Further, second radiological image data of the area of the body of the patient is received, and a radiopaque portion of a synthetic structure to be positioned at the selected biological feature is identified. A location of the radiopaque portion of the synthetic structure relative to the target location is further determined.

In another aspect, the systems and methods described herein include a blood vessel sizing device that has a planar base structure with a front surface and a back surface, with the planar base structure configured to be placed on a user's skin during radiological imaging of a target area of the user, and the planar base structure being substantially transparent to light in the visible spectrum. The device further includes a series of radiopaque positioning markers on the front surface spaced apart along a longitudinal axis of the sizing device. Further, a radiopaque target element is positioned on the front surface, and indicates a dimensional range of a biological feature that is acceptable for positioning of a synthetic structure. The device additionally includes an adhesive layer on the back surface configured to adhere the device to the user's skin.

It is accordingly an advantage of the present disclosure to provide a medical device that simplifies and improves blood vessel size determination and positioning of a device within the blood vessel.

It is a further advantage of the present disclosure to provide a method for improving the process for blood vessel size determination and positioning of a device within the blood vessel.

Additional features and advantages are described herein, and will be apparent from the following Detailed Description and the figures.

BRIEF DESCRIPTION OF THE FIGURES

FIGS. 12A-12B schematically depict a sizing device, according to one or more aspects described herein.

FIGS. 13A-13B schematically depict another implementation of a sizing device, according to one or more aspects described herein.

FIGS. 14A-14B schematically depict yet another implementation of a sizing device, according to one or more aspects described herein.

DETAILED DESCRIPTION

In one example, the present disclosure is directed to medical devices and methods that provide for improved accuracy when positioning of a synthetic structure, such as a MEMS device or a stent, within a biological feature, such as a blood vessel, of a patient. In one implementation, a blood vessel sizing device is configured for placement on the skin of a patient near a feature of interest (e.g. a blood vessel to be imaged). Accordingly, the device may include one or more radiopaque elements, including a target element, and one or more positioning markers having known sizes. When a computer machine generates a radiological image of the blood vessel, the radiopaque elements cause the features of known size to be visible on the generated image (along with the blood vessel image). As such, a clinician may quickly and accurately determine the actual size (true dimension/length) of one or more portions of the blood vessel(s), and identify a portion of a blood vessel suitable for positioning for the synthetic structure.

The terms "graphical representation" and "image" are used herein to refer to an output of an imaging technique. Such imaging techniques that generate the graphical representations/images may include one or more processes (which may not be mutually exclusive, and may be combined with other processes, including non-image based processes), to provide an output comprising a graphical representation or image of a target area and/or target object, including an angiogram, MRI, X-Ray, CT scan, myelogram, thermograph, MRN, ultrasound, and/or combinations thereof or other mechanisms that can produce a graphical representation or image of a target object or target area. Further, those of ordinary skill in the art will readily appreciate that the systems and methods described herein may be utilized for non-biological purposes (e.g. for imaging of synthetic materials, and the like), and without departing from the disclosures herein.

Figure 1:
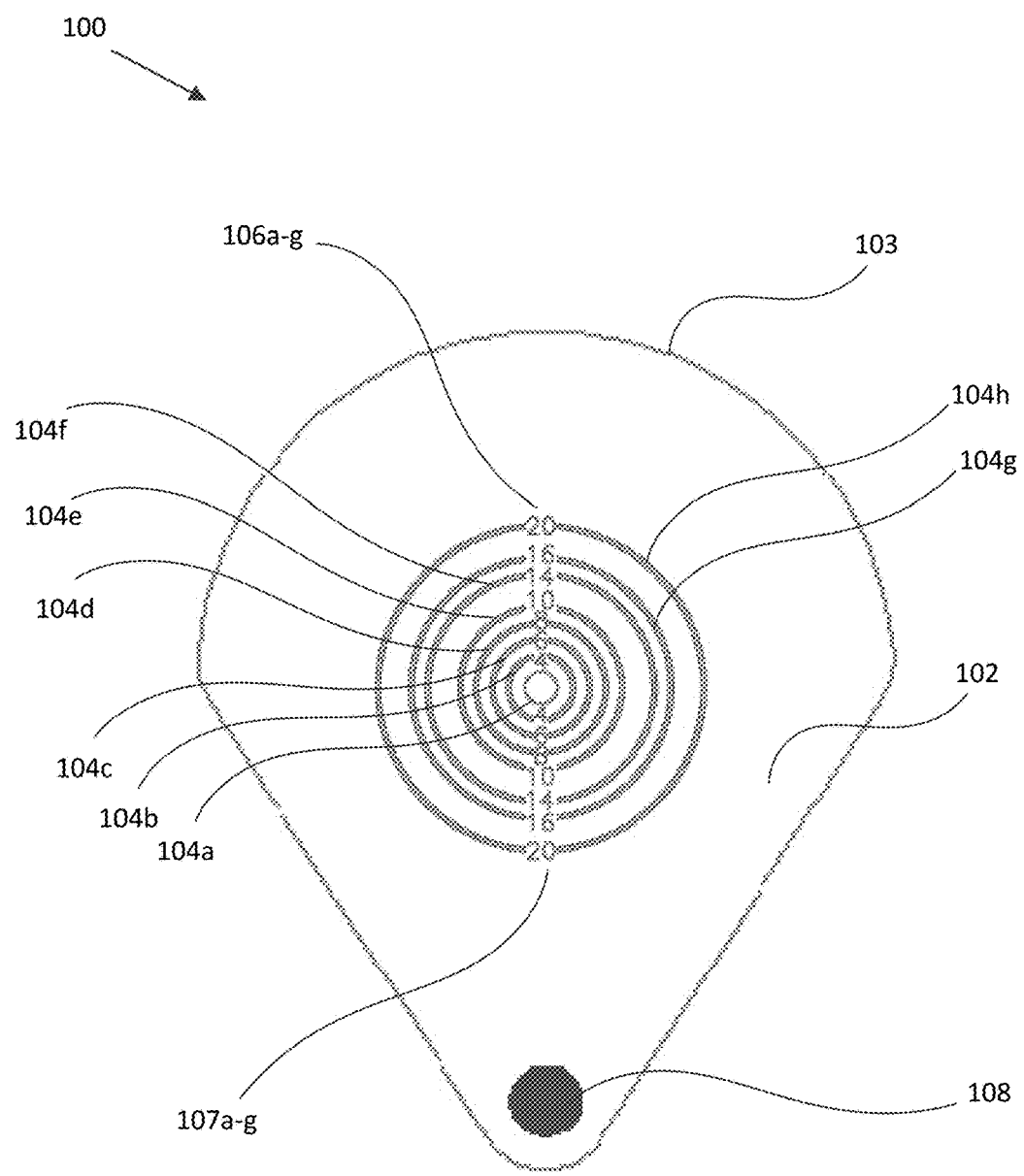
FIG. 1 is a plan view of a blood vessel sizing device.

FIG. 1 schematically depicts a device 100 configured for providing a mechanism to determine one or more dimensions of features in a graphical representation of an imaged object or area. In one implementation, device 100 may be configured to be placed in an area to be imaged, such as, contact with an area of skin of a patient prior to a medical imaging procedure, and such—device 100 may be utilized to determine a true dimension/length of one or more biological features to be imaged using an imaging technique (e.g. an angiogram using x-rays, and the like).

In particular, device 100 may comprise a base structure 102. Positioned on the base structure 102 or another surface are shown a plurality concentric-circle elements, numbered as elements 104a-104h, and a plurality symbols, numbered as symbols 106a-106g and 107a-107g. In one example, the elements 104a-104h, and symbols 106a-106g and 107a-107g, may comprise a radiopaque (radiodense) metal, a radiopaque alloy, or another radiopaque material known to those of ordinary skill in the art, and wherein radiopacity will be readily understood to those of ordinary skill in the art as a property of a material that substantially reduces and/or prevents electromagnetic radiation of a certain wavelength/range of wavelengths from passing through the material. In particular, radiopacity may be understood as a property of a material that substantially reduces and/or prevents x-rays from passing through the material. In yet other embodiments, materials that are reactive to certain imaging techniques or chemical processes may also be utilized. In this regard, the elements and symbols herein (including elements 104, symbols 106 and/or 107) may be configured to reduce or prevent transmission of wavelengths such as to appear opaque. In yet other embodiments, they may contain materials known to contrast with an intended target object or target area, such as would be similar to the use of contrast agents in radiological sciences. In yet another embodiment, at least one element and/or symbol may comprise a material that is configured to fluoresce as a result of being imaged or some mechanism utilized prior to or during the imaging process(es).

In one example, one or more of elements 104a-104h and/or symbols 106a-106g may be provided directly, e.g., printed, onto base structure 102 using, e.g. any appropriate printing method known to those of ordinary skill in the art. In other examples, one or more of elements 104a-104h and/or symbols 106a-106g and 107a-107g may be molded into base structure 102, fastened to base structure 102 by any appropriate fastener, or adhered/welded to base structure 102, and the like.

In one example, base structure 102 may comprise one or more of a polymeric material, a glass, a metal, an alloy, or any other material with material properties that give rise to a contrast between base structure 102 and one or more of elements 104a-104h, symbols 106a-106g and 107a-107g, and/or location marker 108 when imaged using electronic radiation of a particular wavelength/range of wavelengths (e.g., x-rays). In one example, base structure 102 may comprise a polymer that is substantially transparent to electromagnetic radiation in the visible spectrum (e.g. visible light). As discussed above, certain elements (104) or symbols (106,107) may be configured to be opaque and/or react to different imaging processes.

In one implementation, base structure 102 may comprise a material with mechanical properties exhibiting a level of rigidity such that base structure 102 does not readily conform to one or more undulations of a surface onto which it is positioned. In one example, this rigidity may be achieved by selecting base structure 102 with a material thickness corresponding to an appropriate level of rigidity. Specifically, in one example, base structure 102 may comprise a polymeric material with a thickness ranging between 0.2 mm and 2.5 mm, or a thickness of 0.25 mm, 0.5 mm, 0.75 mm, 1.0 mm, among many others.

In one implementation, concentric-circle elements 104a-104h may have known diameters. In one example, the diameters of the elements 104a-104h may measure 2 mm, 4 mm, 6 mm, 8 mm, 10 mm, 14 mm, 16 mm, 20 mm or 30 mm. However, as will be readily apparent to those of ordinary skill in the art, differently sized concentric-circle elements 104a-104h may be used without departing from the scope of this disclosure. Furthermore, a different number of elements than those eight elements represented as 104a-104h may be used on device 100 without departing from the scope of this disclosure. In one example, elements 104a-104h may have a thickness (line thickness) of approximately 0.25 mm, and wherein the diameter of each of the elements 104a-104h is measured to the center of the radiopaque line that makes up each of the elements 104a-104h. In one implementation, and as depicted in FIG. 1, one or more symbols (e.g., symbols 106a-106g and/or 107a-107g) may intersect one or more of the elements 104a-104g. In this way, a symbol may serve as an indicator of a dimensional property of a element with which it intersects. For example, a symbol may denote a radius or diameter of a concentric-circle element with which it intersects. In another example, a symbol may not intersect with an element for which it denotes a dimensional property. In the specific example depicted FIG. 1, a plurality of symbols denote a plurality of diameters of respective concentric-circle elements. Specifically, symbols 106a and 107a are shown as being diametrically opposed on the concentric-circle element 104b, and indicate that concentric-circle element 104b has a diameter of 4 mm. Similarly, symbols 106b and 107b indicate that concentric-circle element 104c has a diameter of 6 mm; symbols 106c and 107c indicate that concentric-circle element 104d has a diameter of 8 mm; symbols 106d and 107d indicate that concentric-circle elements 104e has a diameter of 10 mm; symbols 106e and 107e indicate that concentric-circle element 104f has a diameter of 14 mm; symbols 106f and 107f indicate that concentric-circle element 104g has a diameter of 16 mm; and symbols 106g and 107g indicate that concentric-circle element 104h has a diameter of 20 mm. Yet in another embodiment, one or more elements may have a diameter of 30 mm.

In one example, and as depicted in FIG. 1, symbols 106a-106g are embodied as numerals (e.g. Arabic numerals). In another implementation, different symbols may be used to denote a dimensional property (e.g., a diameter) of one or more of concentric-circle elements 104a-104h. For example, symbols 106a-106g may be computer-readable shapes and/or patterns (e.g. barcodes, and the like). Indeed, in certain embodiments, a symbol or marker may provide computer-readable indicia that may be detected (including automatically) before, during, or after an imaging process. In certain embodiments, the symbol or indicia may not readily convey the dimensional property represented without prior knowledge to its correlation to the dimensional property.

In one implementation, device 100 has a location marker 108, wherein location marker 108. Location marker, like the elements and symbols described herein, may comprise a radiopaque area, contrast materials, and/or fluorescent materials. In one implementation, location marker 108 has a surface area of between 18 and 22 mm². Location marker 108 may be positioned a predetermined distance from at least one or more of elements 104, symbols 106 and/or symbols 107. In one embodiment, the diameter of the a concentric circle, such as circle 104h, may be less than, equal to, or larger than the distance from location marker to that circle, the center of the concentric circles 104a, or another location associated with the circles 104 or symbols 106/107. In yet another embodiment, a dimension (e.g., diameter) of marker 108 may be proportional to one or more aspects of the elements (depicted as circles) 104, and/or symbols 106/107.

In one example, electromagnetic radiation of a certain wavelength (e.g. x-rays) may not pass through, and/or the transmission of the radiation may be substantially attenuated through elements 104a-104h, symbols 106a-106g and 107a-107g, and/or location marker 108. Accordingly, a radiological image (otherwise referred to as a radiograph, or x-ray, and the like) of a biological and/or synthetic feature may include a representation or image corresponding to one or more of elements 104a-104h, symbols 106a-106g and 107a-107g, and location marker 108.

In one implementation, location of one or more of elements 104a-104h, and/or symbols 106a-106g and 107a-107g may be aided by location marker 108, wherein location marker 108 has a comparatively larger radiopaque surface area than any one element (e.g., of elements 104a-104h) or symbol 106a-106g or 107a-107g. As such, the comparatively larger radiopaque surface area of location marker 108 may correspond to a larger feature within a radiological image produced using device 100. Accordingly, location marker 108 may be relatively more visible to a user, and hence, more quickly recognized in a produced radiological image. One or more of elements 104, symbols 106/107, and/or marker 108 may be configured to have a first appearance when imaged under a first imaging process and second appearance when imaged under a second image process. This may be beneficial for a few reasons. In one embodiment, it may allow the detection of whether the proper procedure was used, and/or what type of procedure was used. In one embodiment, the first appearance may be configured to present itself on a graphical representation when a first wavelength was used and the second appearance may be associated with a second wavelength, such as one that may be erroneously used for a specific instance.

FIG. 1 depicts device 100 having base structure 102 with an outer perimeter 103 having a discrete shape. Those of ordinary skill in the art will recognize that base structure 102 (and/or entire device 100) may have any shape, and without departing from the scope of this disclosure. In this way, one alternative implementation of device 200 is depicted in FIG. 2.

Figure 2:
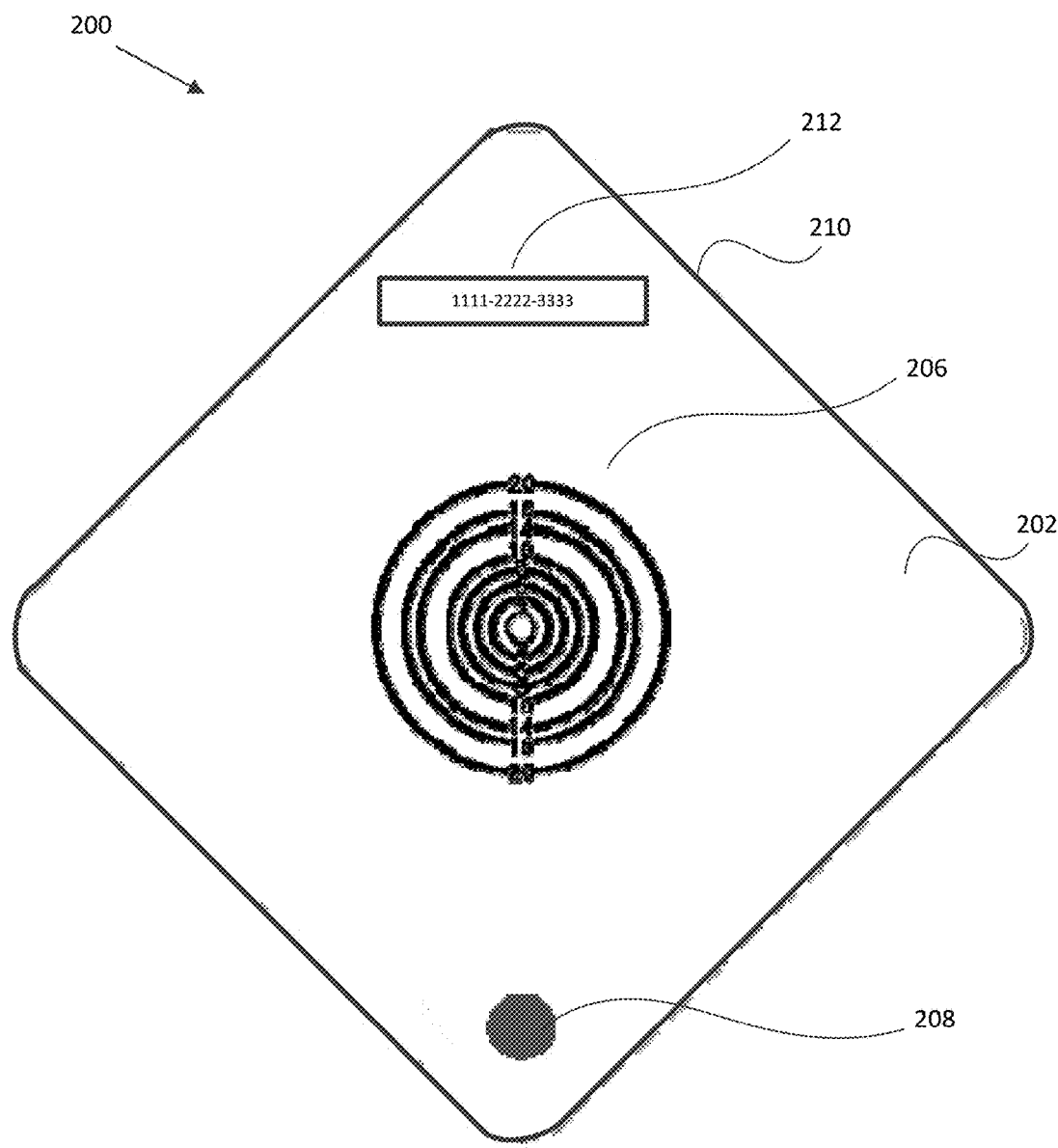
FIG. 2 is a plan view of an alternative implementation of a blood vessel sizing device.

FIG. 2 depicts device 200, which may be similar in one or more aspects to device 100 from FIG. 1. In particular, device 200 has a base structure 202 that may be similar in structural features to base structure 102 from FIG. 1. In this example, base structure 202 is embodied with outer perimeter 210, which exhibits a different shape than outer perimeter 103 of device 100. Device 200 further includes a scale 206 located thereon. In one example, scale 206 may comprise one or more elements like or similar to elements 104a-104h and/or symbols 106a-106g and 107a-107g from FIG. 1, including in relation to one or more of their quantity, size, shape, proportional dimensions, radio opacity, and combinations thereof. Further, location marker 208 may be similar (in terms of dimension, location, and/or other attributes, such as those described above) to location marker 108 from FIG. 1.

One or more devices, such as devices 100 or 200, may include a unique identifier. In one example, device 200 comprises a unique identifier 212. Unique identifier 212 may be provided, e.g., printed, onto base structure 202. In one specific example, unique identifier 212 may comprise a radiopaque material. In one example, unique identifier 212 may be used to associate one or more data points with device 200. For example, unique identifier 212 may be used to identify a patient imaged using device 200 (e.g. to produce, in one example, an x-ray), the specific imaging equipment, personnel employing the imaging technique, date, time, locational information, and combinations thereof, among others. Those of ordinary skill in the art will readily understand that unique identifier 212 may be utilized to associate a device, such as device 100 or device 200, with any type of stored information, wherein the unique identifier 212 itself may store said information, or wherein unique identifier 212 may comprise a sequence of digits and/or symbols that may be used to look up information stored in a collection of information, whether electronic or not, separate from the device 100/200.

Figure 3A:
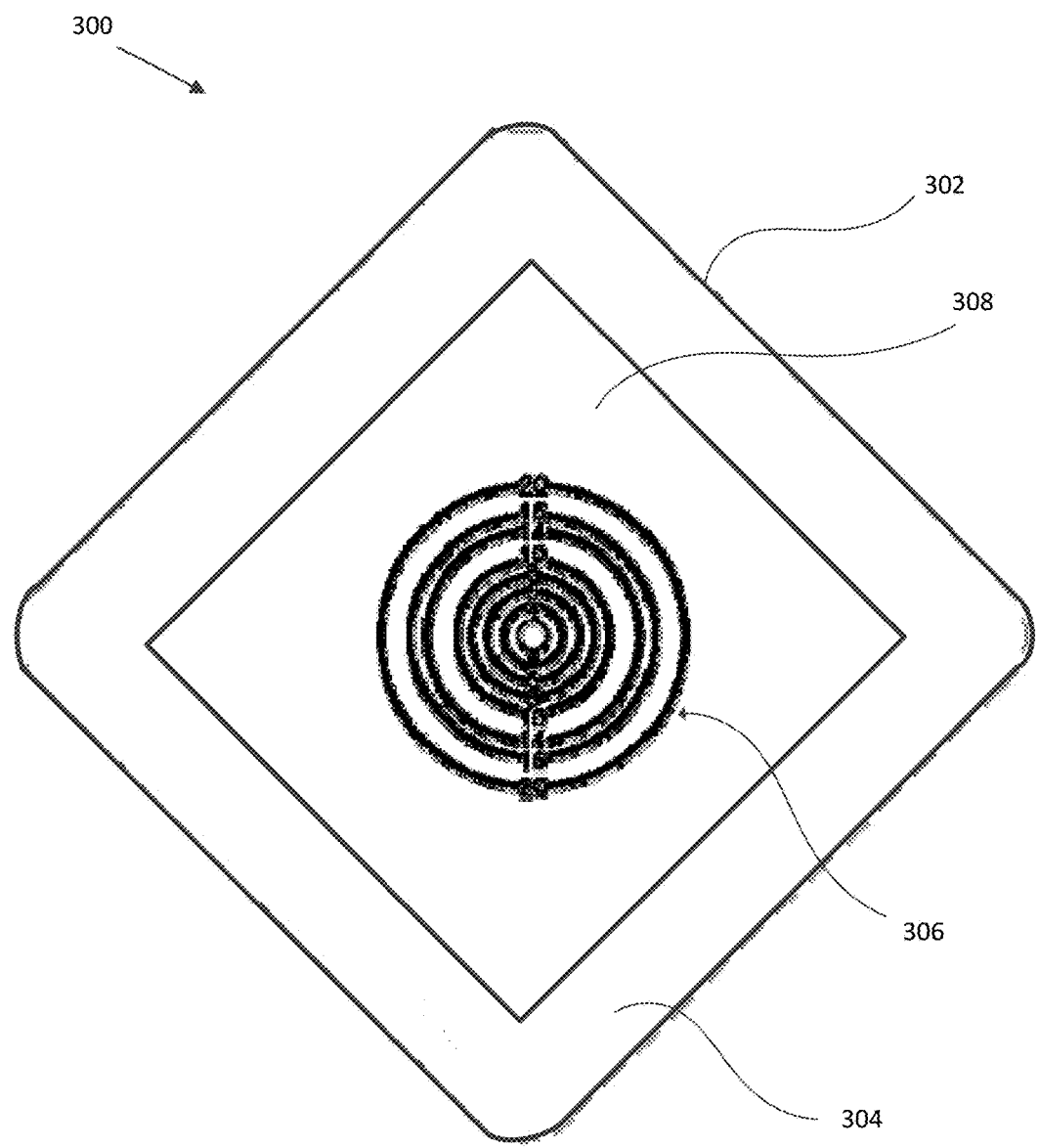
FIG. 3A-3B depicts alternative implementations of blood vessel sizing devices.

FIG. 3A depicts a blood vessel sizing device 300 which may be similar in one or more aspects to one or more of devices 100 and/or 200 from FIG. 1 and FIG. 2, respectively. Device 300 is shown as comprising a base structure 302, wherein, in one example, base structure 302 may be similar to base structure 102 and/or 202 from FIG. 1 and FIG. 2, respectively. Furthermore, device 300 has a scale 306, which may be similar to scale 206 from FIG. 2.

In the example depicted in FIG. 3A, base structure 302 comprises a substantially transparent (e.g. to light in the visible spectrum) polymeric material. Accordingly, this transparency may be utilized when positioning device 300 on an area of skin of a patient and/or other surface (biological or synthetic) prior to an imaging procedure (e.g. an x-ray).

In one example, device 300 may comprise a perimeter area 304, wherein perimeter area 304 may represent an area of the base structure 302 to which one or more of an adhesive layer or a deformable structure (described further in relation to FIG. 4 and FIG. 5) may be affixed. In one example, that adhesive layer and/or deformable structure (not pictured) affixed to perimeter area 304 may be opaque to light in the visible spectrum and/or spectrum of wavelengths utilized by an imaging process. In one implementation in which the perimeter area 304 is opaque to light in the visible spectrum, perimeter area 304 encloses a window 308 of base structure 302, wherein that area of base structure 302 designated as window 308 remains substantially transparent to light in the visible spectrum. As such, window 308 facilitates visual positioning of device 300 on an area of interest prior to an imaging procedure while perimeter area 304 is substantially opaque. In certain embodiments, the perimeter area may be opaque with respect to only one of (a) light in the visible spectrum and (b) spectrum of wavelengths utilized by an imaging process to capture the target object or target area.

It will be readily apparent to those of skill in the art that while perimeter area 304 is depicted in FIG. 3A with a particular shape, many alternative shapes for perimeter area and/or window 308 may be realized without departing from the scope of this disclosure. Furthermore, in another example, perimeter area 304 may cover substantially the same area as base structure 302, and without departing from the scope of this disclosure.

Figure 3B:
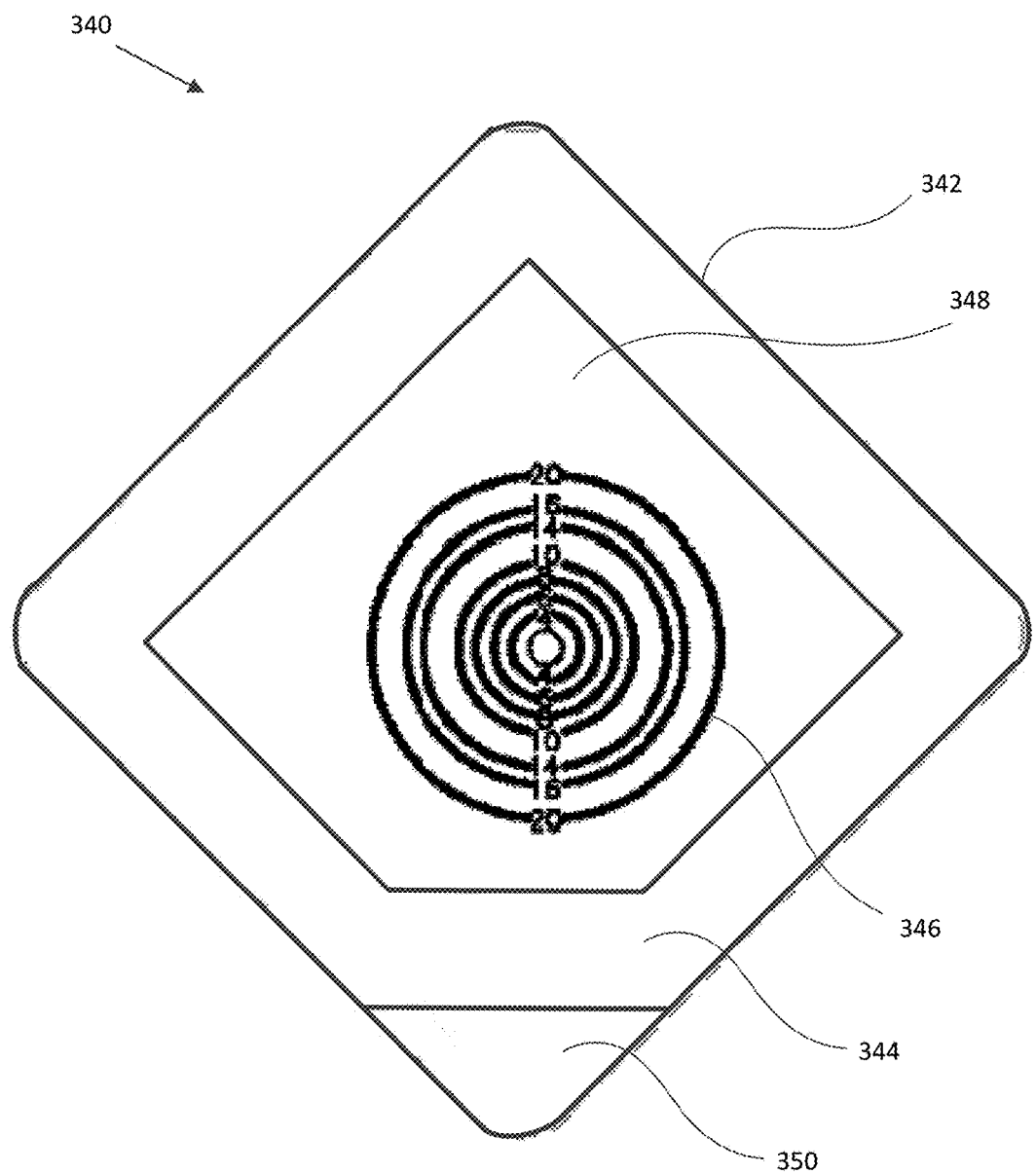

FIG. 3B depicts a device 340, wherein device 340 may be similar to device 300 from FIG. 3A. Similarly to device 300, device 340 may have a substantially transparent base structure 342. Furthermore, base structure 342 may have a perimeter area 344, wherein perimeter area 344 represents an area to which one or more of an adhesive layer and/or a deformable structure may be affixed. Accordingly, perimeter area 344 may be substantially opaque to light in the visible spectrum. As such, visual placement of device 340 on an area of interest may be facilitated by a substantially transparent window 348. It is noted that window 348, and similarly for window 308, while being substantially transparent to light in the visible spectrum, include radiopaque scales 346 and 306, wherein scales 346 and 306 may be substantially opaque to light in the visible and/or x-ray spectrum, among others.

In one example implementation, device 340 comprises a tab structure 350, wherein tab structure 350 may be an area of base structure 342 that is non-adhesive. As such, structure 350 may facilitate removal of device 340 from an area to which device 340 was adhered prior to an imaging procedure. An adhesive layer may be positioned on the entirety of or just a portion of the perimeter area 344.

Figure 4A:
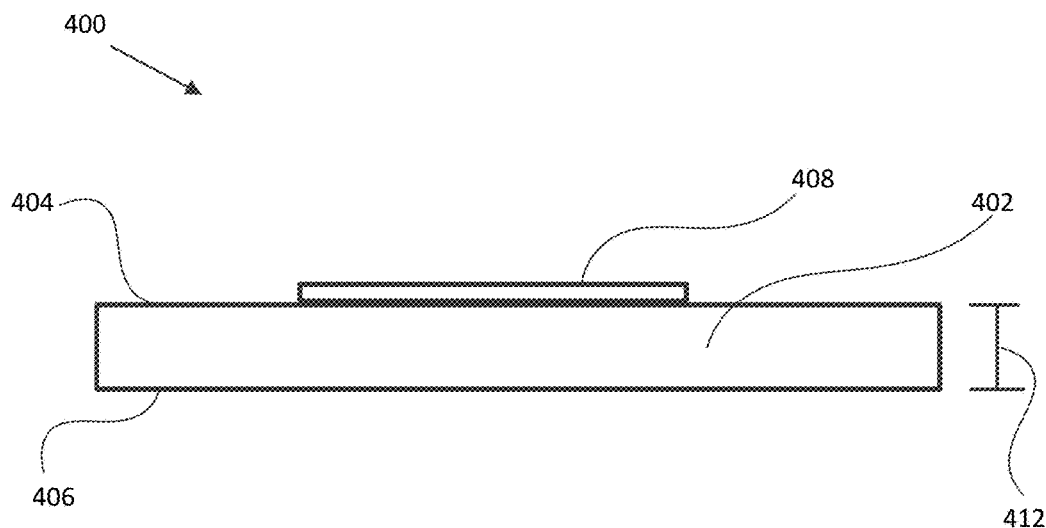
FIG. 4A-4B schematically depict side views of blood vessel sizing devices.

FIG. 4A schematically depicts a side view of an imaging device 400, similar to devices 100, 200, and/or 300 (wherein FIG. 1, FIG. 2, and FIG. 3A-3B depict plan views of devices 100, 200, and/or 300). As such, device 400 comprises a base structure 402 having a front surface 404 and a back surface 406. A scale 408, which may be similar in one or more aspects to scales 206 and 306, is positioned on the front surface 404 of base structure 402. As previously described, scale 408 may be printed, adhered, welded, or joined by any other means known to those of ordinary skill in the art to a surface, such as the front surface 404. The thickness of base structure 402 is represented as thickness 412, and which may range between 0.2 mm and 2.5 mm, and the like.

Figure 4B:
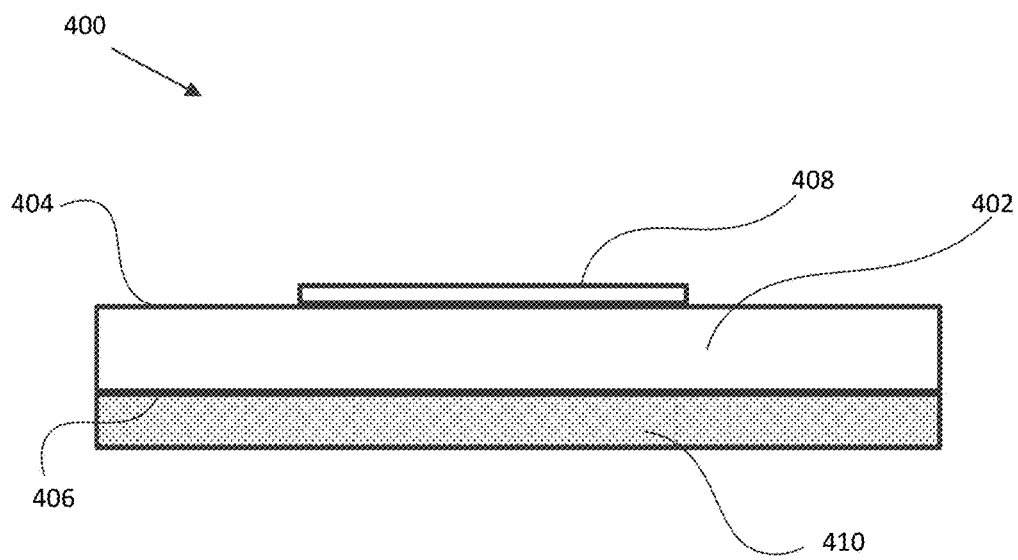

Turning to FIG. 4B, device 400 from FIG. 4A is depicted having an alternative configuration, and including an adhesive layer 410 on the back surface 406 of base structure 402. In one example, adhesive layer 410 may cover the entire surface area of the back surface 406 of base structure 402. In another example, adhesive layer 410 may only partially cover the back surface 406. Specifically, in one example, adhesive layer 410 may cover an outer perimeter area, such as perimeter area 304 from FIG. 3A.

It will be readily apparent to those of skill in the art that adhesive layer 410 may comprise any known adhesive. In one example, adhesive layer 410 may comprise a medical adhesive configured to temporarily and removably bond a structure, such as device 400, to an area of skin of a patient.

Figure 5A:
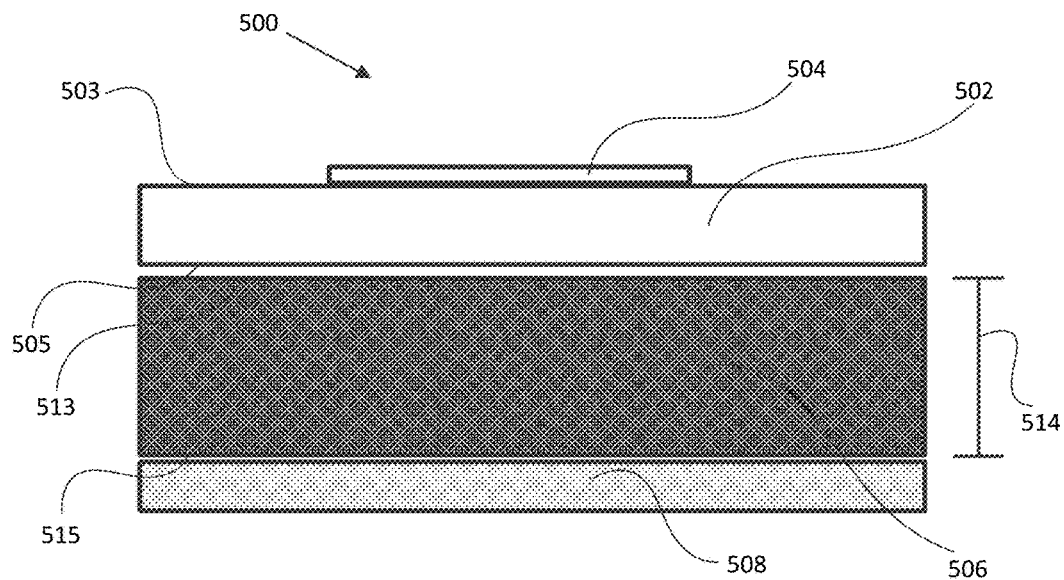
FIG. 5A-5B schematically depict side views of alternative implementations of blood vessel sizing devices having deformable structures.

FIG. 5A schematically depicts device 500. In one example, device 500 may be similar in one or more aspects, to devices 100, 200, 300, and/or 400 previously described. Accordingly, device 500 may comprise a base structure 502, which may be similar to one or more aspects described herein of base structure 102, 202, 302 and/or 402. A scale 504 may be positioned on a front surface 503 of base structure, and a deformable structure 506 may be positioned on a back surface 505 of base structure 502.

As such, a front surface 513 of deformable structure 506 may be adhered to the back surface 505 of base structure 502 by any methodology known to those of ordinary skill in the art, and including, but not limited to, adhesion, molding, fastening, and/or welding, among others. Additionally, an adhesive layer 508, similar to adhesive layer 410, may be positioned on part or all of a back surface 515 of deformable structure 506. It should be understood that deformable structure 506 and adhesive layer 508 may be the same layer. Therefore, discussion of a deformable structure or adhesive layer may be interpreted as a single layer that has both properties.

Deformable structure 506 may comprise a material with physical properties (e.g. hardness) allowing for deformation (compression, and the like) without failure of the material. Accordingly, deformable structure 506 may comprise a sponge-like material which may be a synthetic foam, or any other material with mechanical properties suitable for deformation. Furthermore, in one example, deformable structure 506 may have a thickness 514 ranging between 0.5 mm and 15 mm, or a thickness of 1 mm, 2 mm, 5 mm, 10 mm, 15 mm, among others.

Figure 5B:
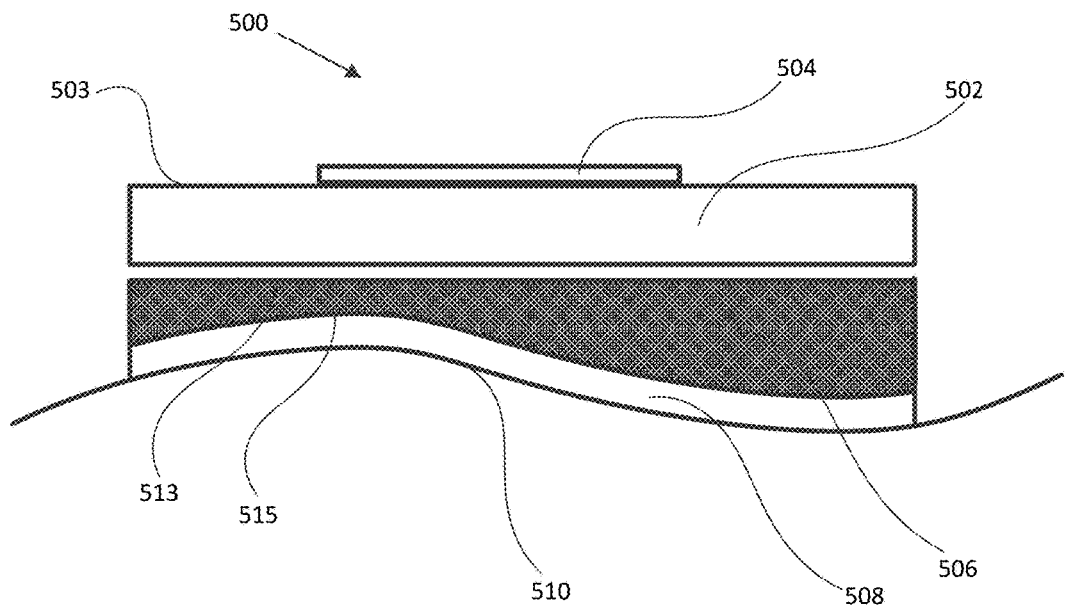

FIG. 5B schematically depicts device 500 adhered to an uneven surface 510. As such, deformable structure 506 is depicted in a compressed state, wherein the back surface 515 of deformable structure 506 conforms to the undulations of uneven surface 510, while the front surface 513 of the deformable structure 506 remains substantially planar. Accordingly, base structure 502 of device 500, in addition to the radiopaque scale 504 thereon, also remain substantially planar while device 500 is adhered to uneven surface 510.

Figure 6A:
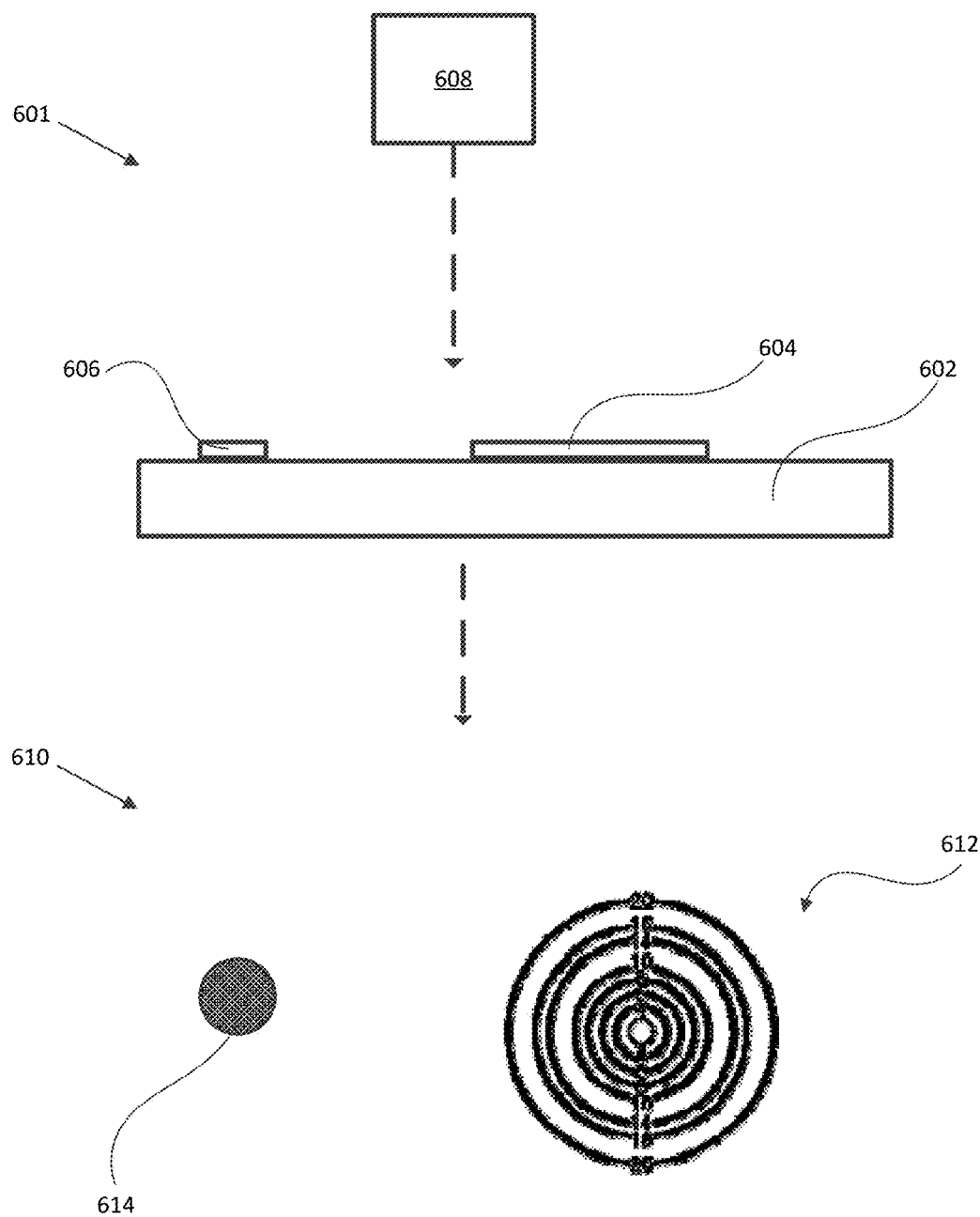
FIG. 6A-6B schematically depict radiographic images produced by blood vessel sizing devices.

FIG. 6A schematically depicts a radiographic image 610 resulting from electromagnetic radiation of a certain wavelength (or range of wavelengths), e.g. x-rays, incident on a device 601 which may be laid over a passageway of a living being, such as a blood vessel of a human. Accordingly, device 601 may be similar in one or more of the aspects described herein to one or more of devices 100, 200, 300, 400, and/or 500. In particular, FIG. 6A schematically depicts a source 608 emitting electromagnetic radiation that is incident upon a base structure 602, a radiopaque scale 604, and a location marker 606 of device 601. In one example, part, or all, of the electromagnetic radiation incident on scale 604 and location marker 606 is absorbed. Yet, other embodiments may have materials that get excited by, or otherwise react to the imaging process or other process used in conjunction with the imaging process. Accordingly, the radiographic image produced upon detection of the electromagnetic radiation transmitted through base structure 602 includes a radiopaque scale image 612 and a location marker image 614.

Figure 6B:
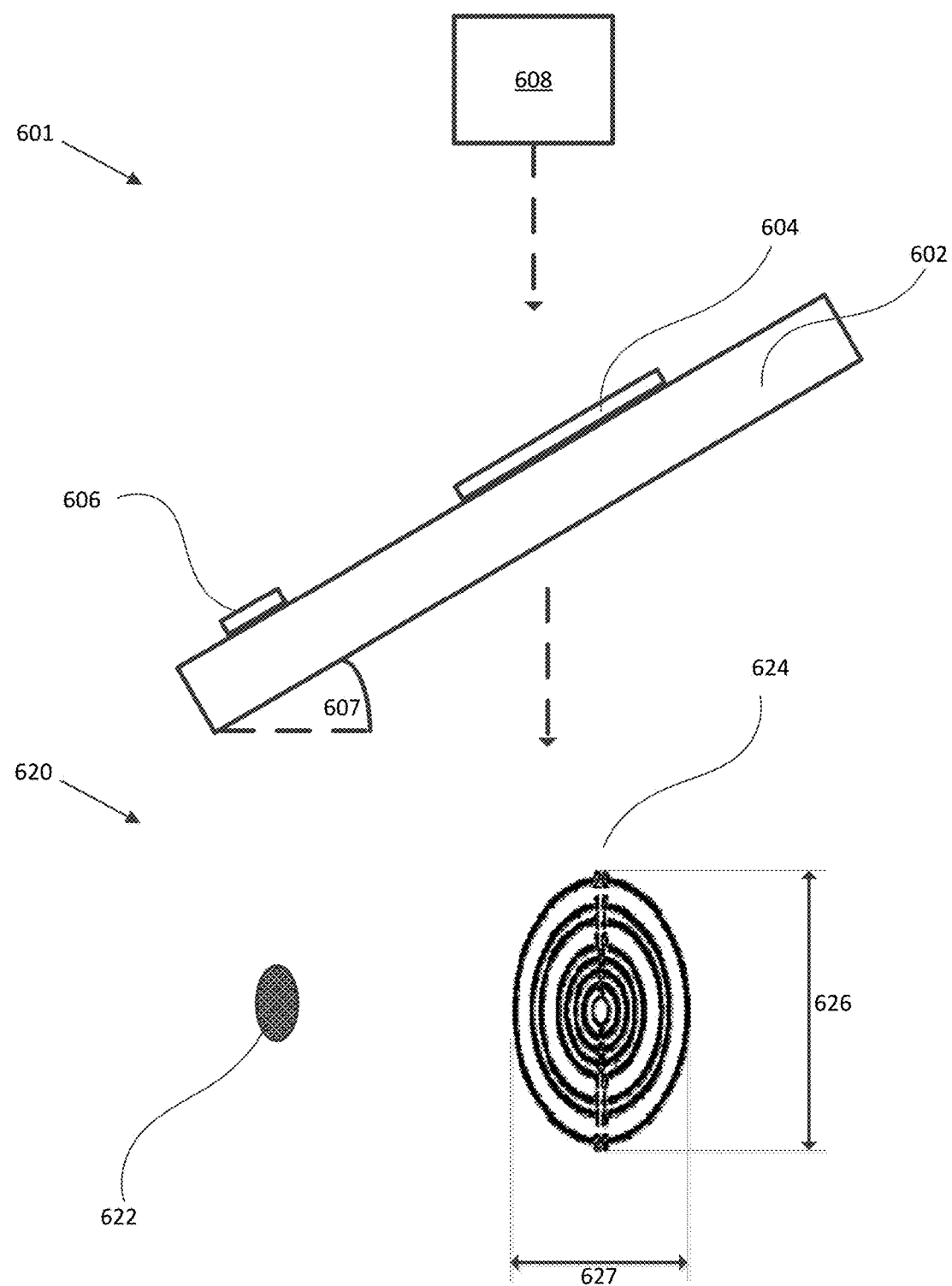

FIG. 6B depicts the same device 601, but angled, at angle 607, with respect to source 608 along a defined plane. Those skilled in the art will appreciate that the device may be angled with respect to the source along multiple planes, however, for sake of understanding aspects of the innovative embodiment, only a single plane is discussed. Because the device 601 is angled with respect to the source, the electromagnetic radiation emitted from source 608 is no longer orthogonal to base structure 602 (electromagnetic radiation now incident upon base structure 602 at an angle of (90°-[angle 607]°. As such, the radiographic image 620 produced as a result of the angle between the incident radiation and device 601 results in a radiopaque scale marker image 624 and a location marker image 622 having ellipsoidal shapes, as depicted.

The distortion of the radiopaque scale marker image 624 and location marker image 622 may be regarded as an error of parallax, wherein, among others, minor axis 627 of radiopaque scale marker 624 no longer represents a true length. However, due to the concentric-circle design of scale marker 604 (e.g. radiopaque concentric-circle elements 104a-104h from FIG. 1), the resulting radiopaque scale marker image 624 includes at least one true length. In particular, the true length of concentric-circle elements 104a-104h is represented in radiopaque scale marker image 624 along the longest axis (major axis) 626 of that ellipsoidal image of radiopaque scale marker 624. As such, a user may determine the longest axis of radiopaque scale marker image 624, and measure one or more true lengths of one or more concentric-circle elements 104a-104h along said axis 626. In this regard, although there are two axes shown (626 and 627), those skilled in the art will realize that any straight line that passes through the center of a concentric circle can serve as an axis. In this regard, the closest axis to the true axis may be set to the nearest degree, of the circle, or nearest half degree or whole number of degrees. Advantageously, device 601, and in particular, the concentric-circle elements 104a-104h, thereby allow a user to avoid errors of parallax.

In one example, device 601 may not comprise a rigid structure. In particular, in one example, base structure 602 may bend in one or more directions. For example, base structure 602 may substantially conform to one or more areas of curvature of the human body onto which it is a fixed. As such, due to bending of base structure 602 along one or more axes, a resulting marker image 624 produced by source 608 may be distorted along multiple axes. For example, distortion of marker image 624 may result in a first major axis associated with the depicted 20 mm (which may be other dimensions, such as 30 mm or 3 cm) concentric circle of marker image 624 (e.g. circle 104h from FIG. 1), and a second major axis associated with, in one example the 10 mm concentric circle of marker image 624 (e.g. circle 104d from FIG. 1), wherein the first and the second major axes are not parallel. As such, in one example, it may be advantageous for a user to determine a concentric circle size, from those concentric circle sizes depicted in marker image 624 (e.g. 2 mm, 4 mm, 6 mm, 8 mm, 10 mm, 14 mm, 16 mm, 20 mm, or 30 cm among others) that most closely matches a dimension of an imaged feature. In this way, a user may identify a first major axis in marker image 624 to be used in association with a first imaged feature, wherein this first major axis is a most accurate axis visible in marker image 624 having a dimension that is close to a dimension to be measured in the first imaged feature.

Accordingly, a user may identify a second major axis in marker image 624, due to distortion of marker image 624 as a result of bending of base structure 602 along one or more axes. As such, the second major axis may not be parallel to the first major axis identified. Accordingly, the second major axis may be a most accurate axis visible in marker image 624 having a dimension that is close to a dimension to be measured in a second imaged feature.

Figure 7:
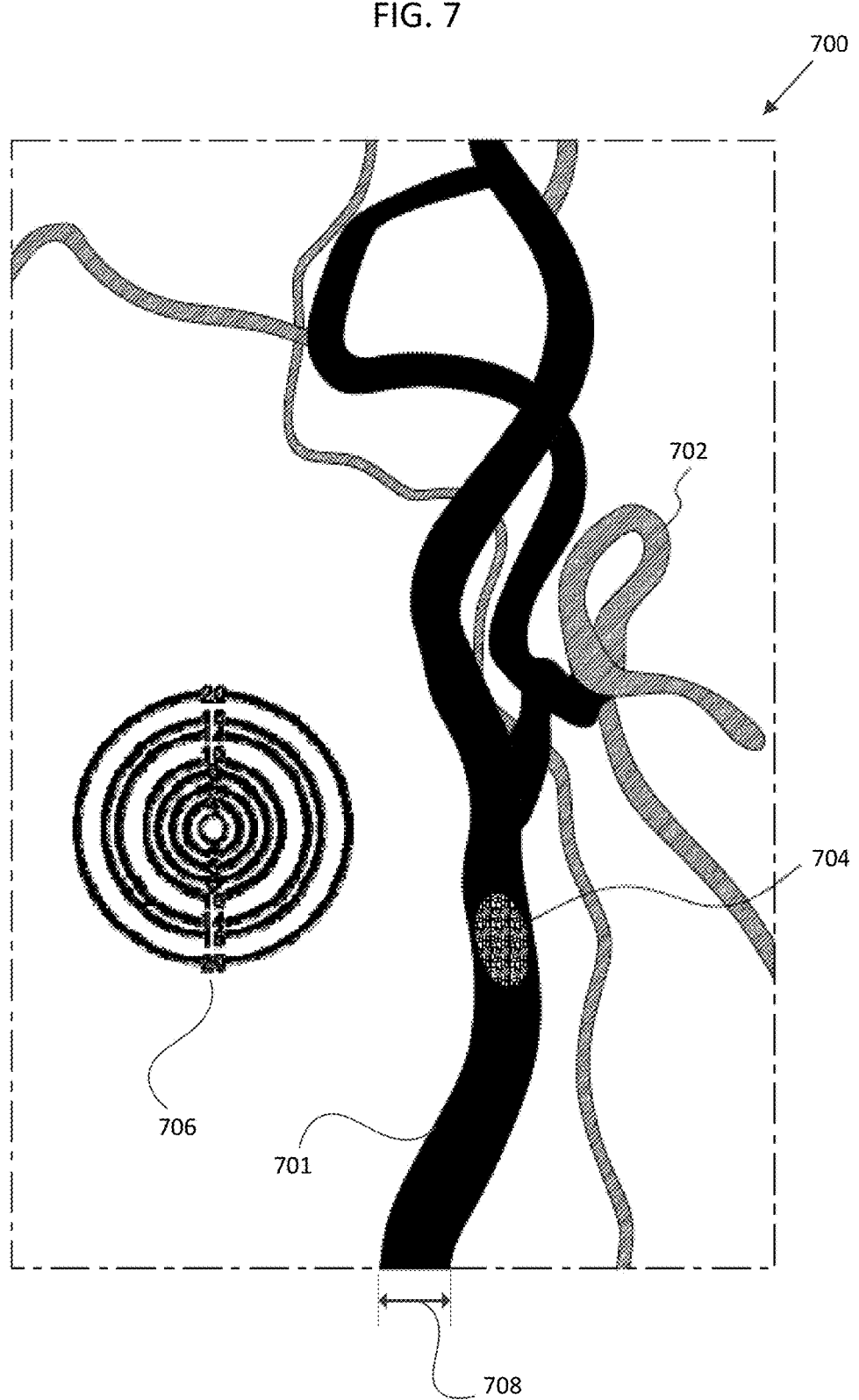
FIG. 7 schematically depicts a radiological image including one or more biological features.

FIG. 7 schematically depicts a radiological image 700, that defined a field of view or target area including one or more biological features (which may include a target object. In particular, the image 700 of FIG. 7 may be an angiogram. Those of ordinary skill in the art will readily understand various methodologies for carrying out an angiogram, which include, among others, use of contrast agents to view blood vessels, and the like. Accordingly, any known technique for angiography or other radiographic imaging may be employed with the systems and methods described herein, and without departing from these disclosures. Furthermore, image 700 may be computer-generated, or may be produced by the detection of electromagnetic radiation (e.g. x-rays) by a film.

FIG. 7 depicts a plurality of blood vessels comprising at least a portion of the carotid artery 701, and one exemplary branching blood vessel is labeled as vessel 702. In one example, it may be desirable to obtain one or more dimensions of biological features from a given radiological image 700. Accordingly, in one example, one or more dimensions of a stenosis 704 may be obtained from radiological image 700. In one implementation, a device, such as device 100, 200, 300, 400, and/or 500 may be positioned on a surface of interest, and within the field of view of a radiological image to be produced. In one specific example, a scale image 706 (which may comprise a plurality of elements and symbols) may be included in a radiological image 700 produced. As such, one or more true dimensions of one or more biological features (e.g. a blood vessel width 708) may be determined using one or more concentric-circle elements of the unknown size (e.g. elements 104a-104h from FIG. 1) of scale image 706.

Figure 8:
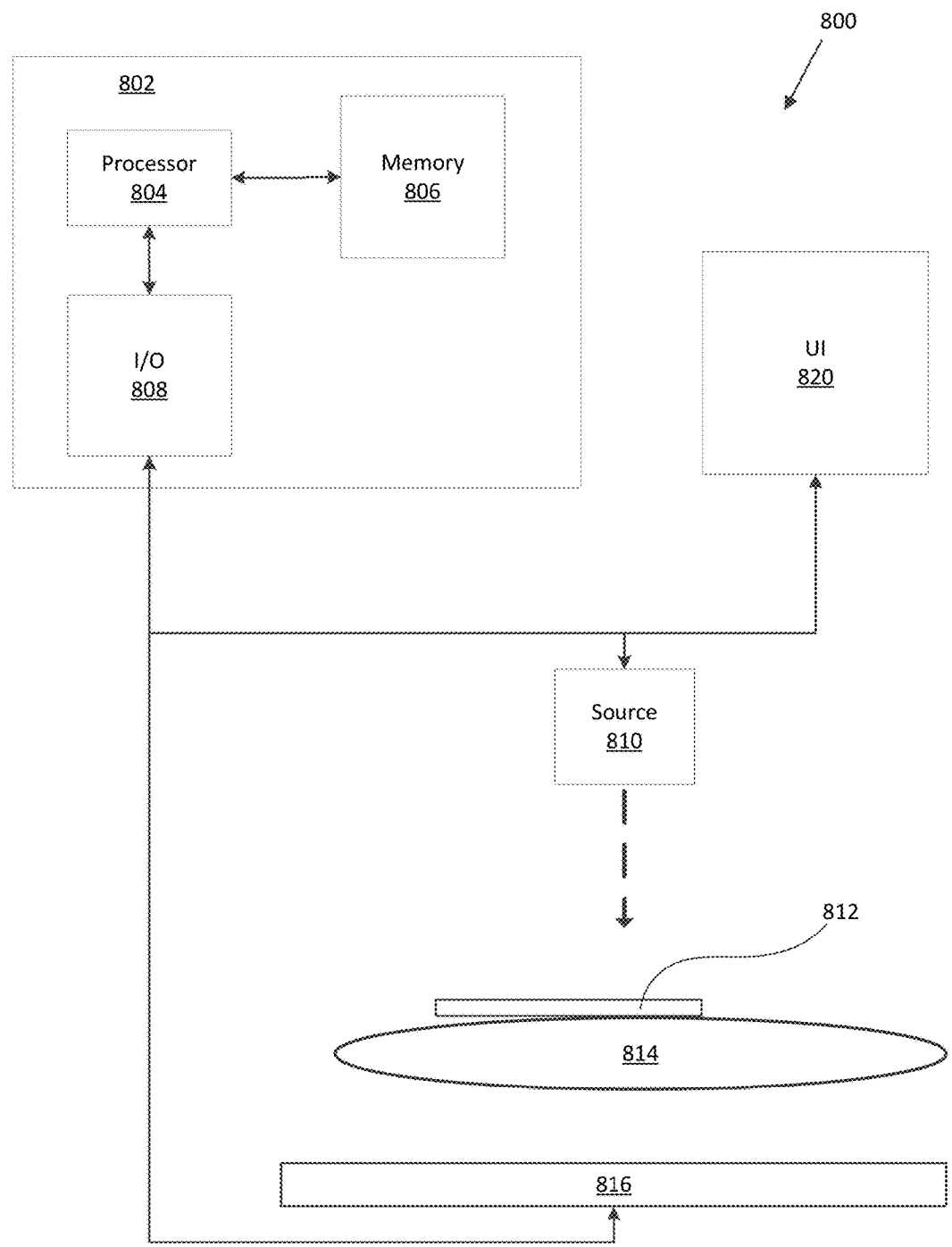
FIG. 8 is a schematic block diagram of an imaging system.

FIG. 8 schematically depicts an imaging system 800. Specifically, system 800 includes a computer 802 having a processor 804, memory 806, and an interface 808. Computer 802 is further connected to a user interface 820, a source 810, and a detector 816. It will be readily apparent to those of ordinary skill in the art that connections between devices 802, 820, 810, and/or 816 may be wired or wireless, and using any known network type and/or communication protocol. For example, communication between one or more of devices 802, 810, 820, and/or 816 may be through a local area network (LAN), a wide area network (WAN), or the Internet, and using a communication protocol including one or more of the Transmission Control Protocol (TCP), the Internet Protocol (IP), or the User Datagram Protocol (UDP), among many others.

Processor 804 may be a general-purpose central processing unit, or a dedicated and specialized processing chip. Processor 804 may contain a single processing core, or multiple cores acting in parallel, and the like. Memory 806 may be volatile or persistent, and may include one or more of read only memory (ROM), random access memory (RAM), a solid state hard drive (SSD), or memory using optical disc media (CD, DVD, and the like), among others. Interface 808 may comprise those hardware and/or software components for connection of computer 802 to one or more devices 810, 820, and/or 816 across a network. Furthermore, user interface 820 may comprise one or more of a display and/or a control interface for receiving instructions from user. Source 810 may comprise a source of electromagnetic radiation (e.g. x-rays) suitable for radiographic imaging. Accordingly, detector 816 may comprise an electronic detection device sensitive to electromagnetic radiation emitted from source 810, and such that the electromagnetic radiation received by detector 816 may be used to construct a digital image.

Element 814 represents an area of skin of a patient to be imaged using source 810 and detector 816. Positioned on said area of skin of a patient 814 is a blood vessel sizing device 812, wherein the device 812 may be similar to one or more of those devices (100, 200, 300, 400, and/or 500) previously described. Accordingly, one or more features of device 812, such as, for example, a radiopaque scale, such as radiopaque scale 408, may be included in a resulting image constructed by computer 802.

In one example, a user of system 800 may identify a biological feature within a radiological image, wherein said image may be a real-time digital image produced by computer 802 from data received from detector 816. For example, a user may identify a one or more passageways (blood vessels) and/or one or more objects within passage ways (blood clots), among others. In one example, it may be desirable for a user to determine a true dimension of one or more biological features present in an image produced by system 800. Accordingly, a user may input one or more instructions, via interface 820, identifying one or more biological features of interest within an image produced by system 800, and visible to a user at user interface 820. Subsequently, one or more identified features of interest may be compared to an image produced by blood vessel sizing device 812, wherein said image may be similar to a scale, such as scale 612, among others. As such, one or more known sizes/dimensions of said scales 612 and/or 624 may be compared to the one or more identified features of interest, and a true dimension may be determined. Furthermore, it will be apparent to those of ordinary skill that blood vessel size or device 812 is agnostic to the type of imaging equipment used, in addition to the magnification and/or specific image manipulation processes applied to the data detected by detector 816.

In one example, a user may manually compare a length property of a biological feature visible within an image produced by system 800 to one or more known dimensions of a radiopaque scale present within said image. For example, a user may measure a width of a blood vessel, as shown in an image produced by system 800, using a calipers. However, due to the magnification/scaling and/or other image manipulation steps carried out on the data received from detector 816, this length measured by the calipers may not be a true dimension of the width of the blood vessel.

Accordingly, the user may compare the length measured by the calipers to one or more concentric-circle elements (e.g. elements 104a-104h from FIG. 1) visible within a radiopaque scale (e.g. radiopaque scale 612 and/or 624), and wherein the radiopaque scale is visible within the same radiological image as the blood vessel of interest (e.g the visible radiopaque scale 612 and/or 624 will have been subject the same scaling and/or other image manipulation processes such that a direct comparison between the length measured with the calipers, and one or more lengths from the radiopaque scale is still possible). In doing so, the user may compare the measured length from the calipers to the major axis (e.g. as discussed in relation to FIG. 6B) of the radiopaque scale, and by comparison to one or more of the known dimensions of the concentric-circle elements, determine a true dimension of the blood vessel width. Furthermore, it will be readily apparent to those of skill that any mechanical measurement device may be utilized for measuring a length property of a biological feature. For example, a user may utilize a ruler, measuring tape, or calipers, among many others.

In another example, one or more true dimensions of an identified biological feature may be determined by an automated process. One example of such an automated process is described in relation to FIG. 9.

Figure 9:
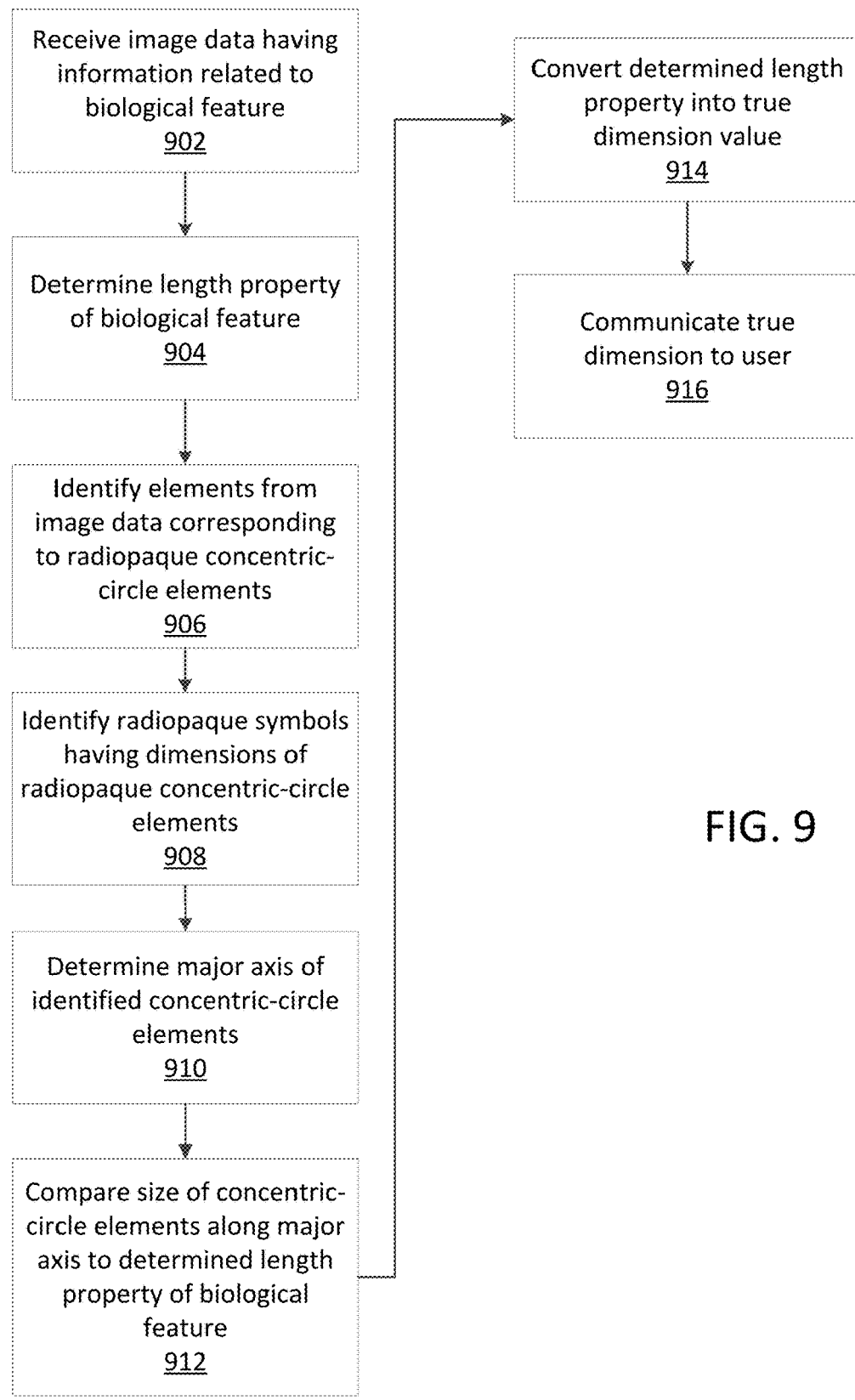
FIG. 9 is a flowchart diagram of one or more processes for automatically determining a true dimension of a future captured in a radiological image.

FIG. 9 is a flowchart that may be implemented in the automatic determination of a true dimension of a feature captured in a radiological image (e.g., radiograph/x-ray). In one example, the description in FIG. 9 may be used in conjunction with imaging system 800 from FIG. 8. Image data may be received from a detector, such as detector 816 (e.g., block 902). In one example, this image data may include information related to one or more biological features (tissues, organs, blood vessels, blood clots, and the like). A dimensional property (e.g., a length property) of the one or more biological features of interest within the received image data may be obtained (e.g., block 904, which may follow block 902).

In an example embodiment, block 904 may represent one or more processes to determine a length of one or more features within a radiological image using an arbitrary length metric (e.g. a number of screen pixels, and the like). In this way, due to one or more scaling and/or other image manipulation processes carried out on the image data used to create the radiological image, a true dimension of the one or more features is not readily known.

One or more elements from image data that correspond to concentric-circle elements, such as those elements 104a-104h from FIG. 1, may be identified (e.g., block 906). Block 906 may occur in the absence of block 904. Those of ordinary skill in the art will readily understand that any computer image recognition processes may be utilized with the one or more processes of block 906, and without departing from the scope of this disclosure.

Symbols, such as for example, 106a-106g and 107a-107g, may be identified from the image data. This may occur before, during, after and/or in absence of blocks 904/906. In accordance with further embodiments, a major axis of one or more identified concentric-circle elements may be determined, such as at block 910. In this way, and as described in relation to FIG. 6B, a longest axis of a radiopaque scale marker image, such as radiopaque scale marker image 624 from FIG. 6B, may be used to read known lengths of one or more concentric-circle elements 104a-104h without an error of parallax (and/or with a statistically significant reduction in an error of parallax.

A dimensional property (e.g., the length property) of a biological feature may be compared to one or more dimensions (e.g., lengths) of concentric-circle elements along the determined major axis of a radiopaque scale marker image, such as radiopaque scale marker image 624. Upon comparison of the determined length property of the biological feature to the corresponding concentric-circle elements of the same length (or interpolating/extrapolating from one or more known dimensions of concentric-circle elements), a true dimension value may be determined. As such, the determined dimensional property (e.g., the length) of the biological feature may be converted into a true dimension value (e.g., block 914).

A true dimension value may be communicated to a user, such as via user interface 820 from FIG. 8, which may occur at example block 916.

Figure 10B:
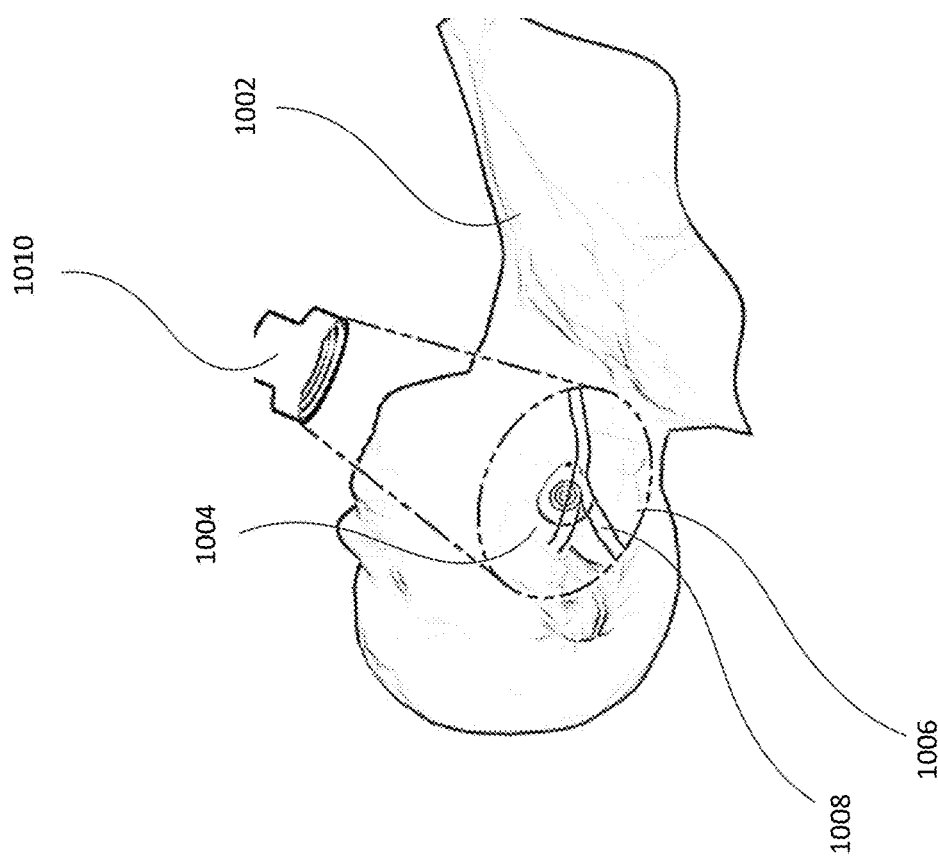
FIG. 10A-10B schematically depict a blood vessel sizing device being used on a human patient.
Figure 10A:
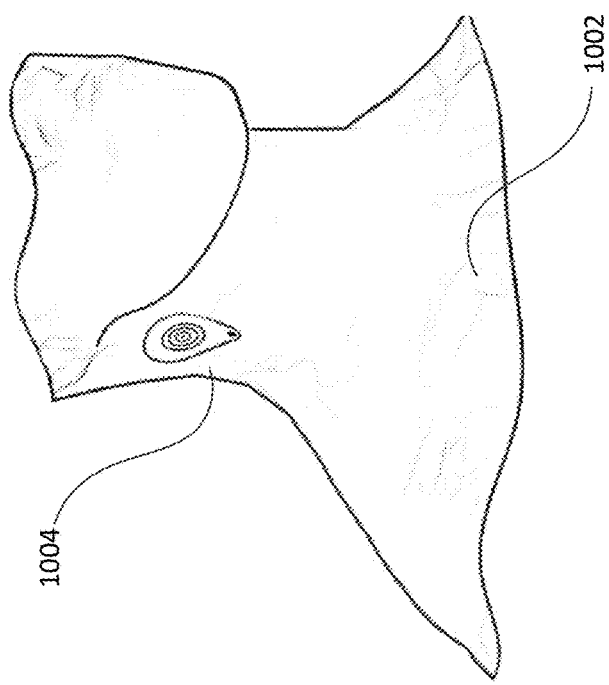

FIG. 10A schematically depicts an example implementation of device 1004 being used. In particular, FIG. 10A schematically depicts device 1004 positioned on a neck area of a human patient 1002. Accordingly, in one implementation, device 1004 may be similar to device 100, 200, 300, or 400, and the like. Following from FIG. 10A, FIG. 10 B schematically depicts patient 1002 being imaged using imaging device 1010. As will be apparent to those of ordinary skill in the art from the foregoing disclosures described herein, imaging device 1010 may be, among others, part of an x-ray device for performing an angiogram. In other implementations, device 1010 may be a part of an MRI device, a CT device, a myelogram device, a thermograph device, an MRN device, an ultrasound device, and/or combinations thereof, among others.

Accordingly, as schematically depicted in FIG. 10B, imaging device 1010 may image a region 1006 that includes both device 1004 and, in one example, blood vessel 1008. In one specific example, blood vessel 1008 may be a carotid artery, among others.

Figure 11A:
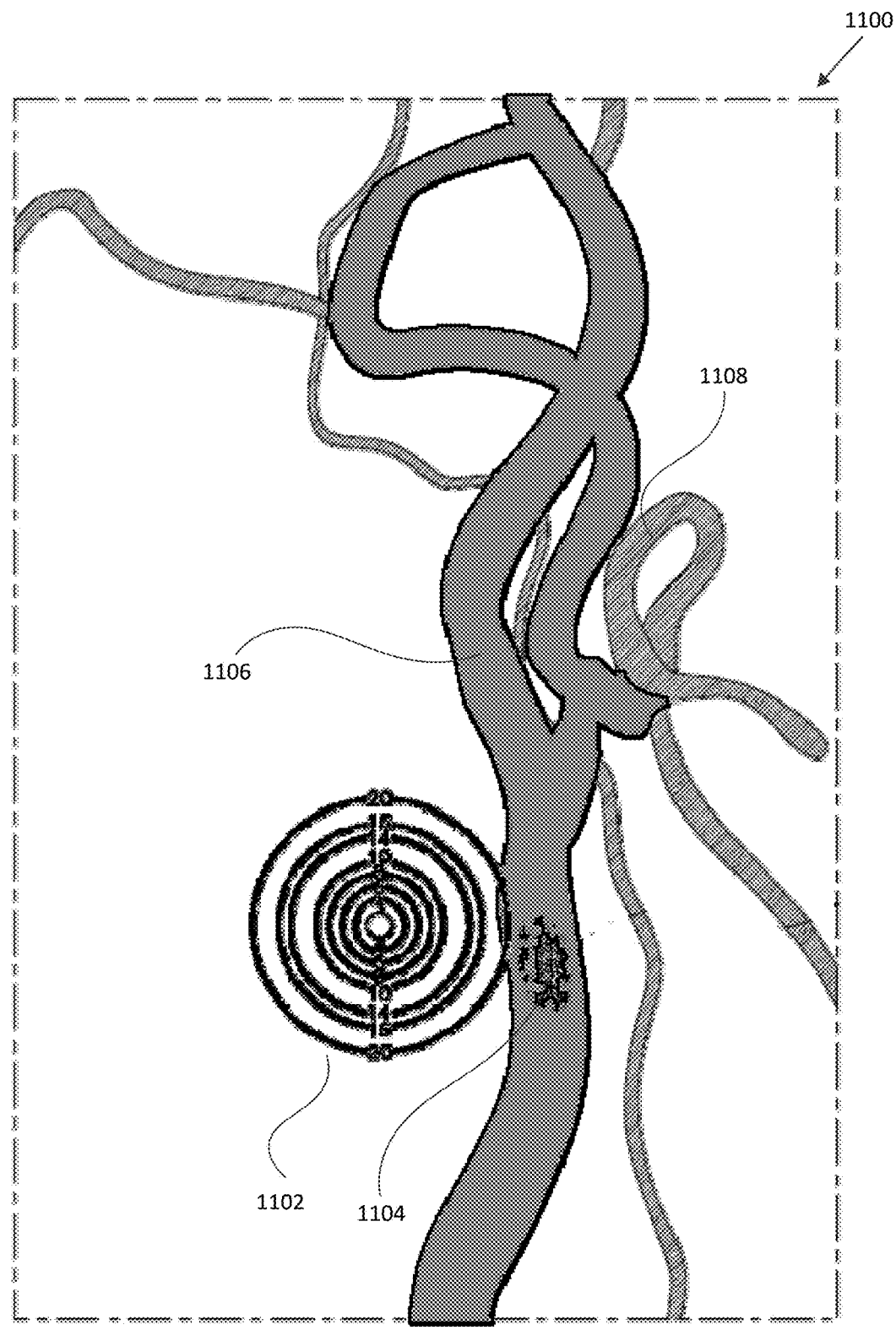
FIGS. 11A-11D schematically depict various implementations of a device that may be utilized for locating an area of interest within a radiological image.

FIGS. 11A-11D schematically depict various implementations of a device that may be utilized for locating an area of interest within a radiological image. In certain embodiments disclosed herein, the device may be used to locate or estimate the location of a feature or area of interest of: (1) a first image of a first area, wherein a first feature is captured under a first image criteria; and (2) a second image that comprises at least the same first area, wherein the same feature is present but not captured or captured to a less degree, under a second image criteria, Non-limiting examples are discussed in relation to FIGS. 11A-11D. In one example, FIG. 11A depicts a radiological image 1100 that includes a scale image 1102, which may be similar to scale image 706, and generated as a result of one or more imaging processes of a device, such as device 100, and the like. Additionally, FIG. 11A depicts a schematic view of a blood vessel 1106 having a feature of interest 1104, which may be, in one example, a stenosis, and the like. Furthermore, FIG. 11A depicts a branching vessel 1108. In one example, vessel 1106 and feature 1104 may be visible within an image (e.g., radiological image) 1100 through use of a contrast agent. In this regard, FIG. 11A may represent a first image of a first area, wherein the feature 1104 may be a first feature that is captured under the specific capturing conditions, such as using a radiograph and contrast agent (or specific type/dosage of agent).

Figure 11B:
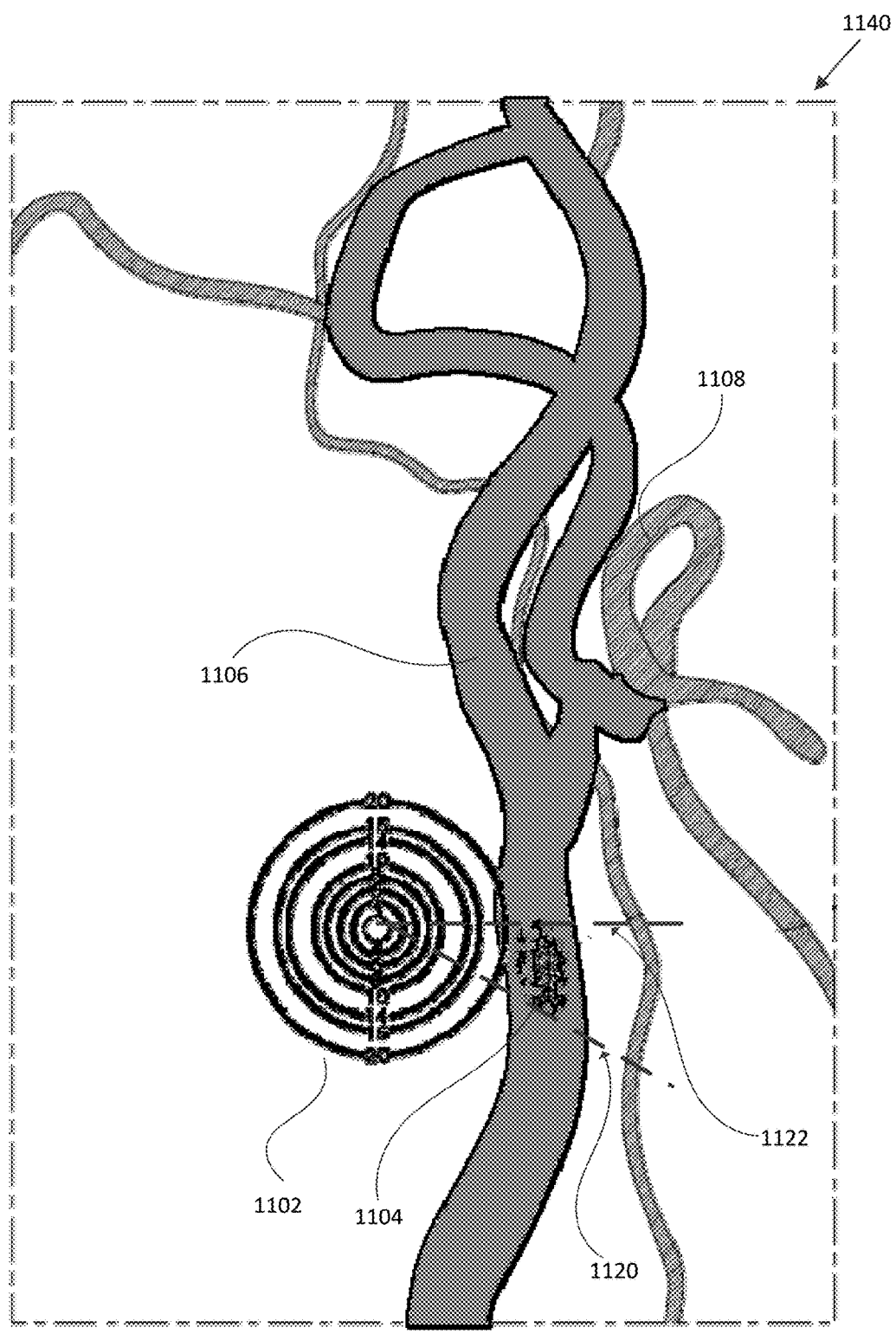

FIG. 11B schematically depicts a radiological image 1140 that is similar to image 1100 from FIG. 11A. In particular, FIG. 11B schematically depicts scale image 1102 being utilized to locate a feature of interest 1104. Specifically, a position of scale image 1102 may be noted relative to feature 1104. Accordingly, those lines 1120 and 1122 may represent imaginary lines, or visible lines depicted on an electronic interface (computer screen) or other representation of image 1140 (e.g. a printed copy of image 1140, and the like) that may be traced out from the center of scale image 1102, and delimiting the ends of feature 1104 within vessel 1106. For example, a user (a clinician or otherwise) viewing image 1140 may note that a "top" end of feature 1104 corresponds to a "3 o'clock position" at an outer concentric-circle element (that largest 20 mm circular element depicted, which may be larger or smaller, including, for example, 30 mm or 3 cm), and delimited by line 1122. Similarly, the user may note that a "bottom" end of feature 1104 corresponds approximately to a "4 o'clock position" at the outer concentric circle of scale image 1102, and delimited by line 1120. As such, while vessel 1106 and feature 1104 are visible in image 1140 through use of a contrast agent, noting a position of feature 1104 relative to scale image 1102 may allow said feature 1104 to be located without using further contrast agent in subsequent images having a same field of view.

In furtherance of this example, those of ordinary skill in the art will readily understand various contrast agents, otherwise referred to as radiocontrast agents, or contrast media, among others, may be used to improve visibility of one or more blood vessels, and associated features, when imaged using x-ray-based imaging techniques. Accordingly, in one example, a contrast agent may be utilized in image 1100 to view vessel 1106, and may include an iodinated (iodine-based) contrast agent, among others. As such, those of ordinary skill in the art will understand that while contrast agents are generally considered safe for use during in vivo imaging, there exist various side effects that may be associated with the use of contrast agents. For example, contrast agents may have a detrimental impact upon kidney function, or may, in some instances, lead to higher rates of blood clotting, among others. As such, it may be desirable for an imaging process to reduce an amount of contrast agent utilized to, in one example, image a vessel for positioning of a stent, among others. Thus, a second image (which may be a subsequent frame in a live video capture) may be the same area and feature (e.g., feature 1104), however, blood flow has moved the contrast agent, and as such, feature 1104 may be less visible or not visible.

Figure 11C:
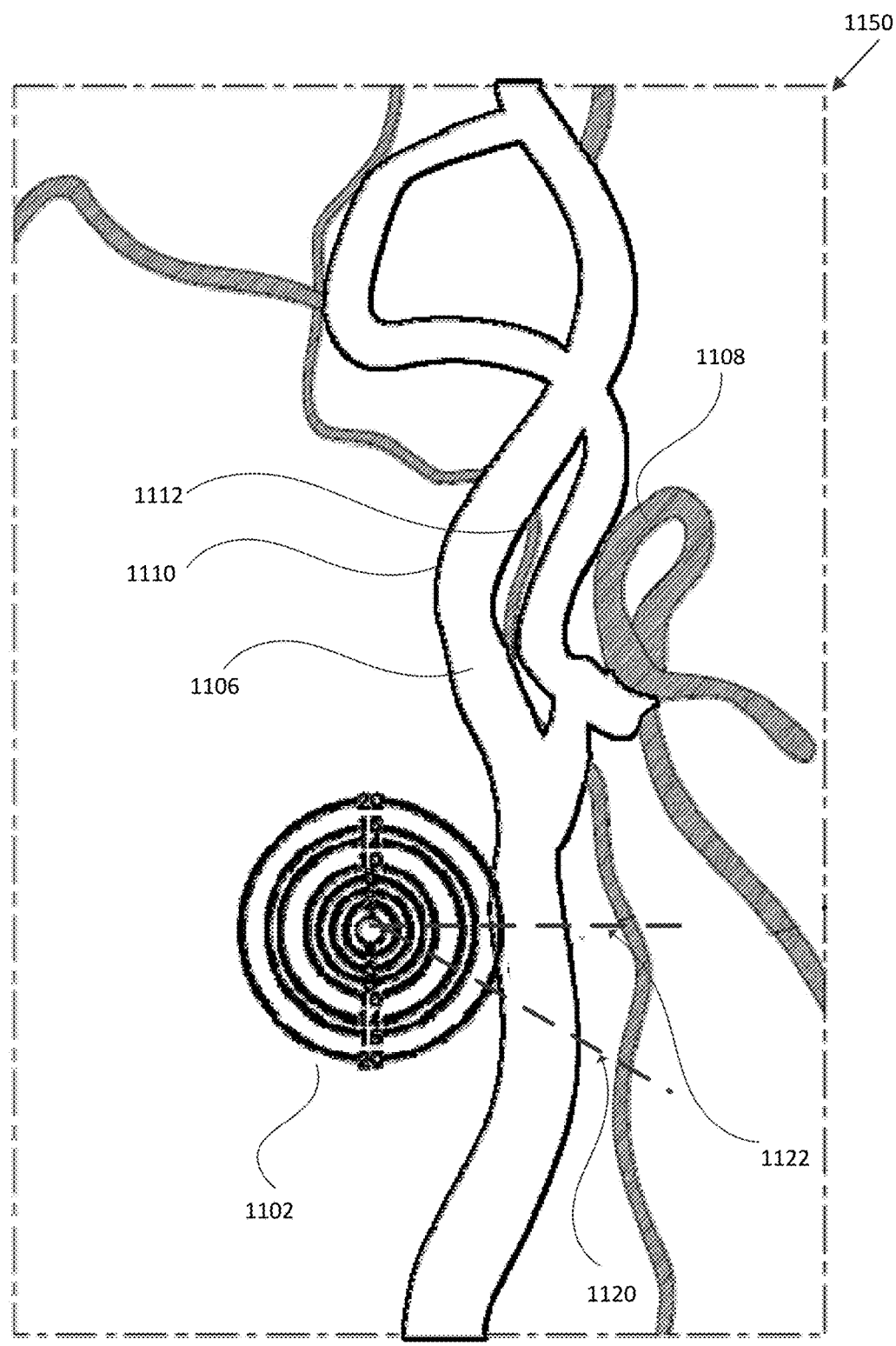
Figure 11D:
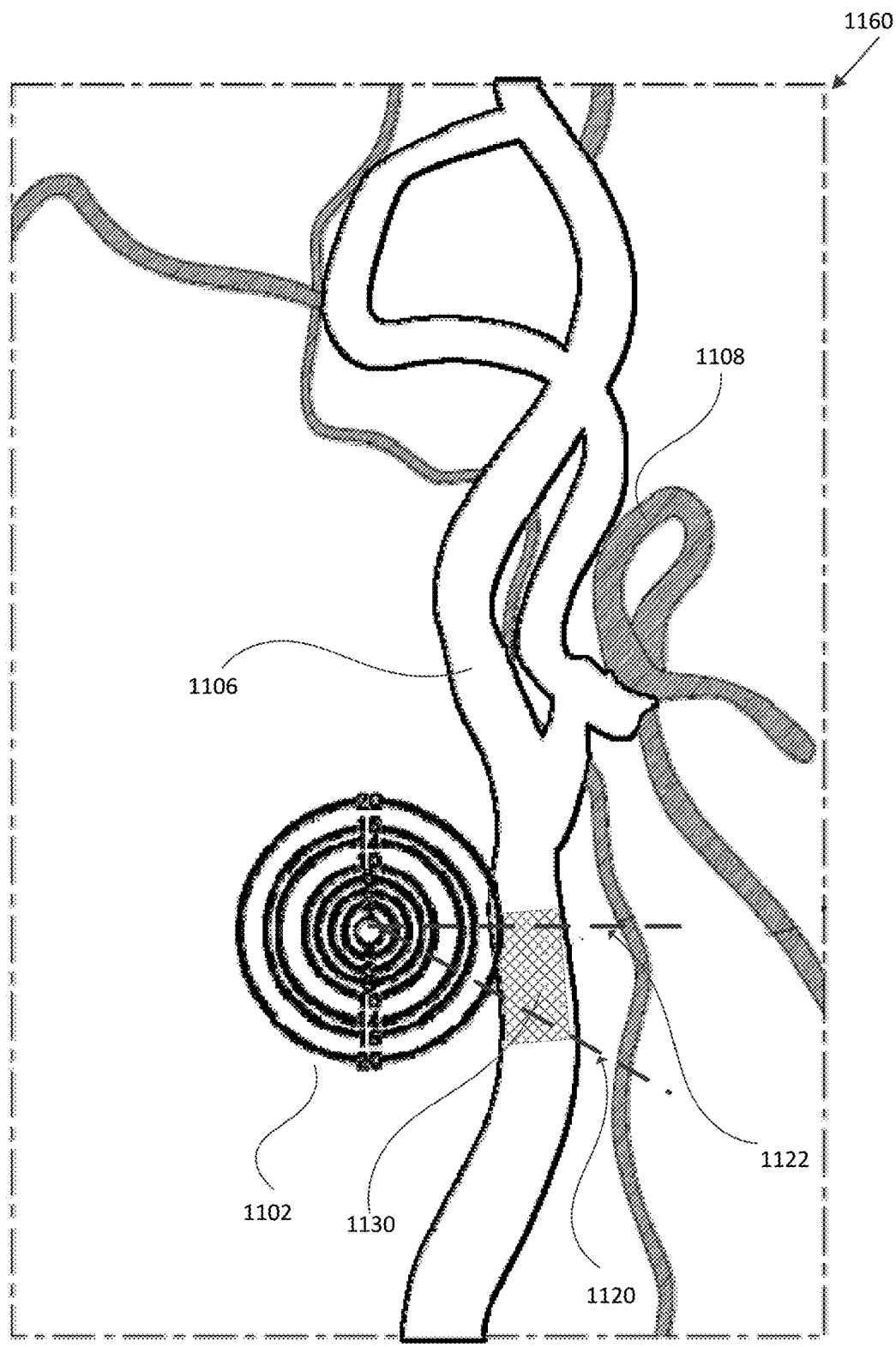

FIG. 11C schematically depicts scale image 1102 being utilized to locate a feature within a vessel 1106 without using contrast agent. As such, respective to FIG. 11A, FIG. 11C may be considered a second image that comprises at least the same first area, wherein the same feature is present but not captured or captured to a less degree, under a second image criteria (e.g., no or less contrast agent). In one embodiment, at least a portion of the vessel itself may be the feature that is less visible or not visible in the second image (or any image that is not the first image). In particular, an outline of vessel 1106 is depicted in FIG. 11C, having a first side wall 1110, and a second sidewall 1112. However, sidewalls 1110 and 1112 outlining vessel 1106 are included for clarity within radiological image 1150. As such, sidewalls 1110 and 1112 represent one or more lengths of blood vessel 1106 that were previously visible within the radiological image 1140 from FIG. 11B through use of a contrast agent, but which may no longer be visible, or may have diminished visibility, within radiological image 1150 due to an absence of a contrast agent. As such, it may be assumed that sidewalls 1110 and/or 1112 of the vessel 1106 are not clearly visible within radiological image 1150 in accordance to one embodiment. However, having noted the position of feature 1104 (which also may not be visible or is of reduced visibility relative to scale image 1102 from FIG. 11B), lines 1120 and/or 1122 may be utilized to locate, approximately, feature 1104 (from FIG. 11B) within image 1150. As such, lines 1120 and/or 1122 may be utilized to position, in one example, a stent, at the feature of interest 1104 from FIG. 11B, and without using, or using a reduced amount of a contrast agent. Turning to FIG. 11D, stent 1130 may be positioned in image 1160 relative to scale image 1102, and utilizing that relative positioning noted using lines 1120 and/or 1122, and the like. Specifically, stent 1130 may be moved into an area of vessel 1106 (vessel 1106 may not be clearly visible within image 1160 due to absence of contrast agent, and the like) by positioning relative to lines 1120 and 1122.

Those of ordinary skill in the art will understand that images 1100, 1140, 1150, and/or 1160 may be still images, or may be "live" images that are periodically updated. In one example, one or more of said images may be updated as a frame rate of six frames per second, however those of ordinary skill in the art will understand that any update/refresh rate may be utilized without departing from the scope of these disclosures. Additionally, those of ordinary skill in the art will understand that's images 1100, 1140, 1150, and/or 1116 may be generated using any appropriate imaging technology including, among others, computed tomography and/or radiography, among many others.

FIG. 12A schematically depicts an example sizing device 1200, according to one or more aspects described herein. In particular, the sizing device 1200 has a base structure 1202. In one example, the base structure 1202 may be planar, and may be configured to be placed on a user's skin during radiological imaging of a target area of the user. Further, the base structure 1202 may be similar to one or more of base structure 102 of device 100, base structure 202 of device 200, base structure 302 of device 300, base structure 402 of device 400, base structure 502 of device 500, and/or 602 of device 600. Additionally, the sizing device 1200 may include a series of positioning markers 1204a-1204t and a target element 1206. The series of positioning markers 1204a-1204t may be uniformly/equally spaced apart from one another (with the exception of markers 1204c and 1204d) along a longitudinal axis of the device 1200 that is parallel to arrow 1208. In one example, a spacing between an adjacent two of the positioning markers 1204a-1204t may measure 10 mm. However, any spacing value may be utilized, without departing from the scope of these disclosures. In the specific example depicted in FIG. 12A, the target element 1206 is centered at a halfway point between positioning markers 1204c and 1204d. However, the target element 1206 may be positioned between other markers in the series 1204a-1204t, or replace the first or last positioning marker within the series 1204a-1204t, without departing from the scope of these disclosures. Further, the sizing device 1200 may be embodied with less than or more than the depicted positioning markers 1204a-1204t, without departing from the scope of these disclosures.

In one example, the series of positioning markers 1204a-1204t and the target element 1206 may comprise one or more radiopaque materials. As such, the series of positioning markers 1204a-1204t and the target element 1206 may utilize a material similar to those described in relation to elements 104a-104h, 106a-106g and 107a-107g from FIG. 1, scale 206 from FIG. 2, scale 306 from FIG. 3A, scale 346 from FIG. 3B, scale 408 from FIGS. 4A and 4B, scale 504 from FIGS. 5A and 5B, and/or scale 604 from FIGS. 6A and 6B, among others.

FIG. 12B schematically depicts a more detailed view of a portion of the sizing device 1200 of FIG. 12A, according to one or more aspects described herein. In particular, FIG. 12B schematically depicts a portion of the base structure 1202, and positioning markers 1204a, 1204b, 1204c, and 1204d, with the target element 1206 spaced between positioning markers 1204c and 1204d. In the depicted example, each positioning marker (e.g. positioning marker 1204a) includes a readable symbol 1208 and a notch 1210 associated with the readable symbol 1208. In the depicted example of FIG. 12B, the symbols (e.g. 1208) associated with positioning markers 1204a, 1204b, 1204c, and 1204d include Arabic numerals. However, in other implementations, different symbols may be utilized. For example, readable symbol 1208 may include computer-readable shapes and/or patterns (e.g. barcodes, and the like), without departing from the scope of these disclosures.

In one example, the target element 1206 includes a central marker 1212 that is centered at a point equidistant to positioning markers 1204c and 1204d. Additionally, the target element 1206 includes a radiopaque ring 1214 that has an inner diameter 1216 and an outer diameter 1218. In one example, the inner diameter 1216 and an outer diameter 1218 may indicate a minimum and a maximum size (e.g., either recommended, absolute, acceptable, or other dimensions for positioning of a synthetic structure (e.g. a MEMS device) within a biological feature (e.g. a blood vessel) of a patient. For example, the acceptable dimensions may represent the acceptable diameter of a blood vessel within an imaged area to receive a medical device. However, the target element 1206 may utilize any dimensions, which may be chosen for any purpose, without departing from the scope of these disclosures. Where described herein, a MEMS device may include, among others, a micro-electromechanical systems (MEMS) sensor device that may be utilized to measure blood pressure and/or blood flow rate of a patient, and/or to communicate related data wirelessly to a remote computer device (e.g. computer device 802). As such, this MEMS device may be positioned within a blood vessel of a user that meets one or more criteria, which may include a blood vessel diameter criteria (which may be visually conveyed with target element 1206 or a portion thereof). In one specific example, a specific MEMS device may be deployed in a blood vessel having a diameter measuring between 7 mm and 10 mm. However, it is contemplated that this disclosure should not be limited to this diameter range, and any sizing constraints may be utilized, without departing from the scope of these disclosures.

The target element 1206 may additionally include symbols 1220 and 1222 indicating the size of the inner diameter 1216 and the outer diameter 1218 of the radiopaque ring 1214, respectively. In the specific example depicted in FIG. 12B, the inner diameter 1216 and the outer diameter 1218 may measure 7 mm and 10 mm, respectively, as indicated by symbols 1220 and 1222. However, any dimensions may be utilized, without departing from the scope of these disclosures. Additionally, symbols 1220 and 1222 may include additional or alternative symbols to those Arabic numerals depicted in FIG. 12B.

In one example, the target element 1206 may be located between positioning marker 1204c and positioning marker 1204d such that the distance 1224, corresponding to the distance between the center of the target element 1206, and the first positioning marker 1204a in the series of positioning markers, indicates a length of a synthetic structure (e.g. a MEMS device), or a portion thereof, to be positioned within a biological feature (e.g. a blood vessel) of a patient.

In one example, the length 1224 may correspond to a length of a synthetic structure, whereby the length of the synthetic structure may not be fully visible within a radiological image as a result of a portion of the synthetic structure not being radiopaque. As such, the positioning of the target element 1206 spaced apart from the first positioning marker 1204a may, in one example, indicate to a user that a synthetic structure is longer than it appears in a radiological image. Thus, targeting element 1206 (as well as others envisioned herein) may be utilized as relative locational devices with respect to features captured within radiographic data, sizing guides with respect to one or more biological features, such as blood vessels for receiving a specific device, as well as positional devices to ensure devices and/or portions thereof that may not be readily visible in the radiographic data are properly guided and/or placed.

In another implementation, the target element 1206 may include one or more concentric circles similar to those described in relation to elements 104a-104h, symbols 106a-106g, and 107a-107g from FIG. 1.

FIG. 13A schematically depicts another implementation of a sizing device 1300, according to one or more aspects described herein. The sizing device 1300 may be similar to sizing device 1200 from FIG. 12A, and include a base structure 1302 similar to the base structure 1202, and a series of positioning markers 1304a-1304t. The positioning markers 1304a-1304t may be equally spaced apart from one another along a longitudinal axis of the device 1300 that is parallel to our 1308. In one example, a spacing between an adjacent two of the positioning markers 1304a-1304t may measure 10 mm. However, any spacing value may be utilized, without departing from the scope of these disclosures. Similar to the positioning markers 1204a-1204t, positioning markers 1304a-1304t may comprise one or more radiopaque materials.

The sizing device 1300 may additionally include a target element 1306. In the depicted example, the target element 1306 is positioned before the first of the positioning markers 1304a. This target element 1306 is more clearly depicted in FIG. 13B, which schematically depicts a more detailed view of a portion of the sizing device 1300 of FIG. 13A, according to one or more aspects described herein.

In one example, the target element 1306 includes multiple concentric circular shapes and symbols similar to elements 104a-104h, 106a-106g and 107a-107g described in relation to FIG. 1.

In one implementation, the target element 1306 may be positioned with its center spaced away from the first positioning marker 1304a by distance 1310. Further, distance 1310 may be equal to the distance 1312 between positioning markers 1304a and 1304b. As previously described, this distance 1310 and/or 1312 may be equal to 10 mm, but may be embodied with any length, without departing from the scope of these disclosures.

It is further contemplated that the target element 1306 may be positioned between two of the positioning markers 1304a-1304t, similar to target element 1206 described in relation to FIGS. 12A and 12B. Further, distance 1310, may, in another example, not be equal to distance 1312. In yet another example, the spacing between one or more of positioning markers 1304a-1304t and/or positioning markers 1204a-1204t may not be uniform. As such, the spacing may, in one example, be logarithmic, among others.

FIG. 14A schematically depicts another implementation of a sizing device 1400, according to one or more aspects described herein. Sizing device 1400 includes a base structure 1402 similar to base structures 1202 and 1302 described in relation to sizing devices 1200 and 1300, respectively. Further, the sizing device 1400 includes a series of positioning markers, of which positioning markers 1404a-1404c are an exemplary sub-set. These positioning markers 1404a-1404c may be similar to positioning markers 1204a-1204t and 1304a-1304t described in relation to sizing devices 1200 and 1300. The sizing device 1400 includes a target element 1406, which may be similar to target element 1206 and/or target element 1306, as previously described. The sizing device 1400 further includes a device deployment guide 1408, which may be utilized by comparing the device deployment guide 1408 to a radiological image of a synthetic device (e.g. a stent, not depicted). The device deployment guide 1408 is further described in relation to FIG. 14B.

FIG. 14B schematically depicts a more detailed view of a portion of the sizing device 1400 from FIG. 14A, according to one or more aspects described herein. In particular, FIG. 14B schematically depicts a portion of the base structure 1402, positioning markers 1404a-1404c, target element 1406, and a portion of the device deployment guide 1408. In the depicted implementation of FIG. 14B, the center of the target element 1406 is aligned with a centerline of the device deployment guide 1408 such that a user may utilize the target element 1406 to quickly determine a desired deployment diameter of the synthetic device (e.g. a stent) that the device deployment guide 1408 represents. It is contemplated, however, that the target element 1406 may not be aligned with a centerline of the device deployment guide 1408, without departing from the scope of these disclosures.

In one implementation, the device deployment guide 1408 may comprise one or more radiopaque materials, similar to the positioning markers 1404a-1404c, and the target element 1406. In one specific implementation, the device deployment guide 1408 may depict a pattern of one or more structures of a stent when expanded/deployed to a correct configuration. As such, the stent pattern depicted by the device deployment guide 1408 may be compared to a radiological image of a stent being inserted into a blood vessel of a patient. As such, when the pattern of the device deployment guide 1408 matches, or is within a range of, a received image of a deployed stent, a user may determine that the stent has been deployed to a correct configuration.

In one embodiment, the depicted image from the radiopaque materials is configured to depict a specific medical device, such as a stent. In one embodiment, a specific model of a stent may be depicted. A specific medical device (e.g., a stent) may have a specific pattern that is discernable in radiographic images when a placed in a specific arrangement, such as when correctly placed within a patient. For example, in one embodiment, element 1408 may depict a replica of properly placed Supera stent, commercially available from Abbott Laboratories, Abbott Park, Ill. In one embodiment, element 1408 may depict a stent or other device having an interwoven design such that the depicted element shows a pattern (which may be the overlaying pattern) when the device is correctly placed. Thus, when imaged, the pattern will be show the correct pattern in accordance with aspects herein. In one embodiment, the length of the depicted stent (or other depicted device) is to scale, such that a stent to be positioned within a blood vessel of a patient may be adjusted to match the depicted length, and thereby facilitate correct deployment.

In an alternative implementation, it is contemplated that the device deployment guide 1408 may include one or more images corresponding to one or more additional or alternative synthetic devices intended to be deployed within a biological feature (e.g. a blood vessel) of the patient. As such, the device deployment guide 1408 may depict a MEMS device, or a portion thereof, among others.

Figure 15A:
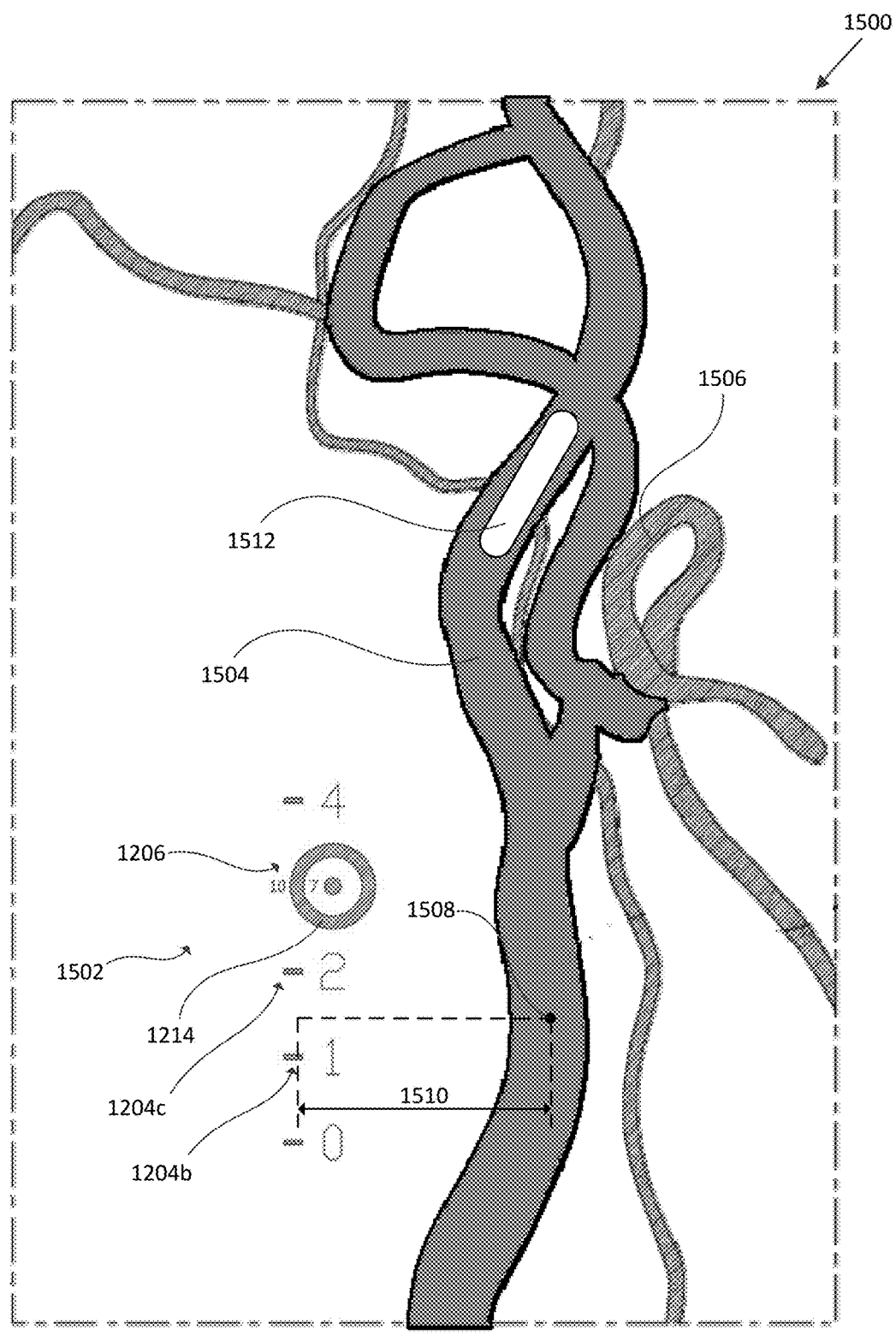
FIGS. 15A-15B schematically depict radiological images that include images of a sizing device, according to one or more aspects described herein.
Figure 15B:
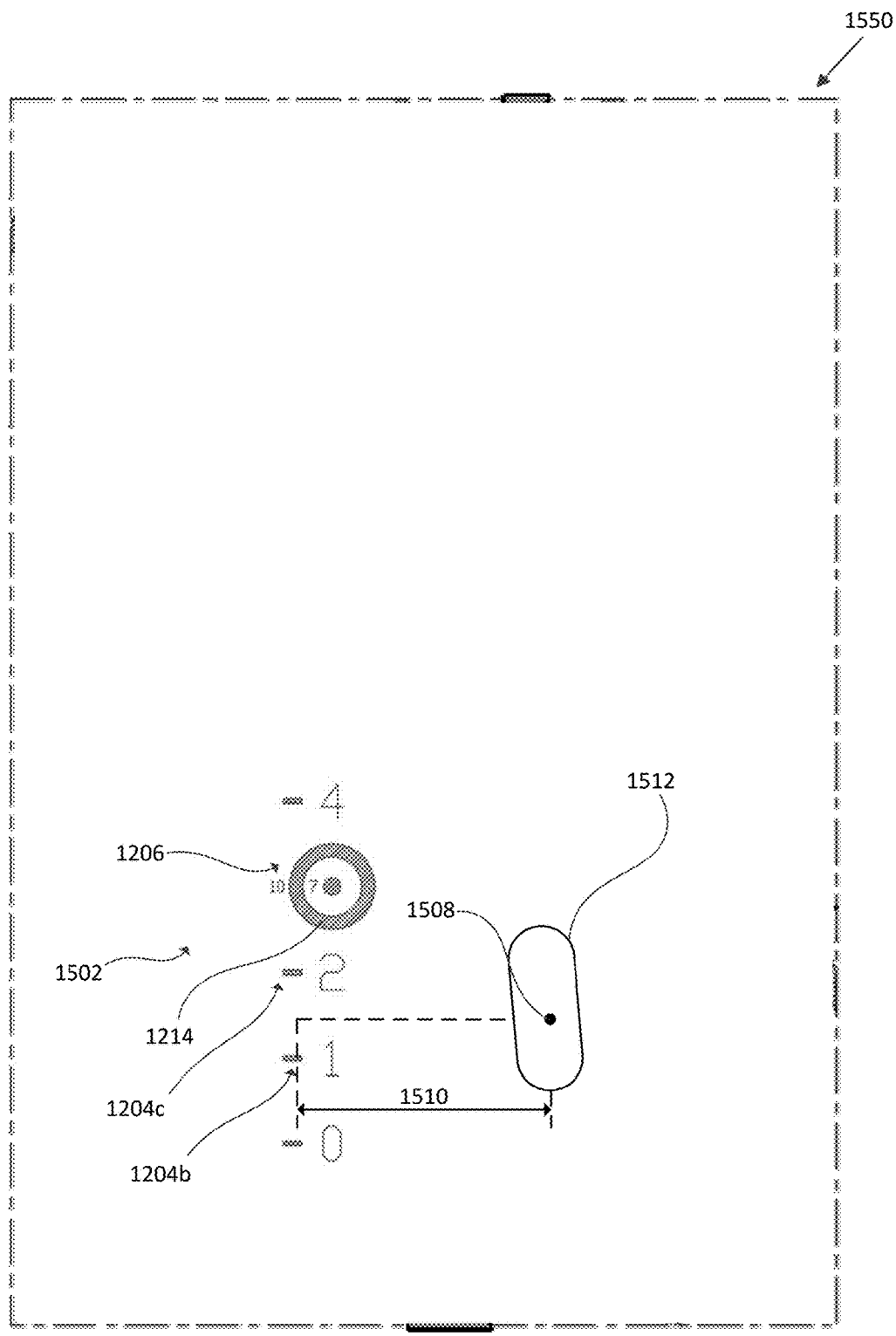

The sizing devices 1200, 1300, and 1400 may be configured to be utilized in a similar manner to device 500 described in relation to FIGS. 5A and 5B, device 601 described in relation to FIGS. 6A and 6B, and/or device 812 described in relation to FIG. 8. Accordingly, one or more of sizing devices 1200, 1300, and/or 1400 may be utilized during radiological imaging, as described in further detail in relation to FIGS. 15A-15B FIG. 15A schematically depicts a first radiological image 1500 that includes an image of a sizing device 1502, according to one or more aspects described herein. In one example, the image of the sizing device 1502 may be generated by utilizing the sizing device 1200 during radiological imaging, among others. FIG. 15A further depicts a schematic view of a blood vessel 1504 and a branching blood vessel 1506. It is contemplated that the blood vessels 1504 and 1506 are visible within the schematic first radiological image 1500 by introducing a contrast agent into the vessels while capturing one or more radiological images (e.g. x-rays, among others). As such, in the depicted schematic example of FIG. 15A, a radiopaque portion of the sizing device 1200 appears within the image 1500 as sizing device image 1502. As previously described, the sizing device 1200 may be utilized to, in one example, position a synthetic structure/device (e.g. a MEMS device) within a biological feature (e.g. a blood vessel) of a patient (it is contemplated that the systems and methods described herein may be utilized with human patients, as well as with animals, without break from the scope of these disclosures).

In one example, computer 802, may identify the sizing device image 1502 within the radiological image 1500. In another embodiment, a user may facilitate the identification. Yet in another embodiment, the user may identify the image, such as to the computer 802. Further, the user and/or processes may identify the target element 1206, and compare the size of the radiopaque ring 1214 to one or more portions of the blood vessel 1504. A suitably-sized portion of blood vessel 1504 may be identified at position 1508 (it is contemplated that other criteria for blood vessel suitability may be utilized in addition to, or as an alternative to, blood vessel size, without departing from the scope of these disclosures). The location of position 1508 may be manually or automatically recorded relative to, in the depicted example, positioning markers 1204b and 1204c (e.g. the identified position 1508 may be identified as falling approximately halfway between positioning markers 1204b and 1204c, and at a distance 1510 away from the centerline of the series of positioning markers 1204a-1204t).

In one implementation, it is contemplated that one or more processes may be executed to overlay digital graphics on the radiological image 1500 marking the location of position 1508. In another example, a user may manually draw overlaid graphics (computer-generated or otherwise) on the radiological image 1500 marking the location of position 1508.

FIG. 15A further schematically depicts a synthetic structure 1512 (e.g. a MEMS device 1512) that is being moved through the blood vessel 1504 and is in an un-deployed configuration. It is contemplated that the structure 1512 may be moved within the blood vessel 1504 using a catheter, or another device (not depicted), without departing from the scope of these disclosures.

FIG. 15B schematically depicts a second radiological image 1550 of the same field of view from FIG. 15A, according to one or more aspects described herein. Accordingly, FIG. 15B schematically depicts the same area of the patient's body as FIG. 15A, but since a contrast agent is not used while capturing the image data used to produce image 1550, blood vessels 1504 and 1506 are not visible, or have reduced visibility. However, using the positioning information calculated from FIG. 15A, the synthetic structure 1512 may be deployed at the selected position 1508, as depicted.

Figure 16:
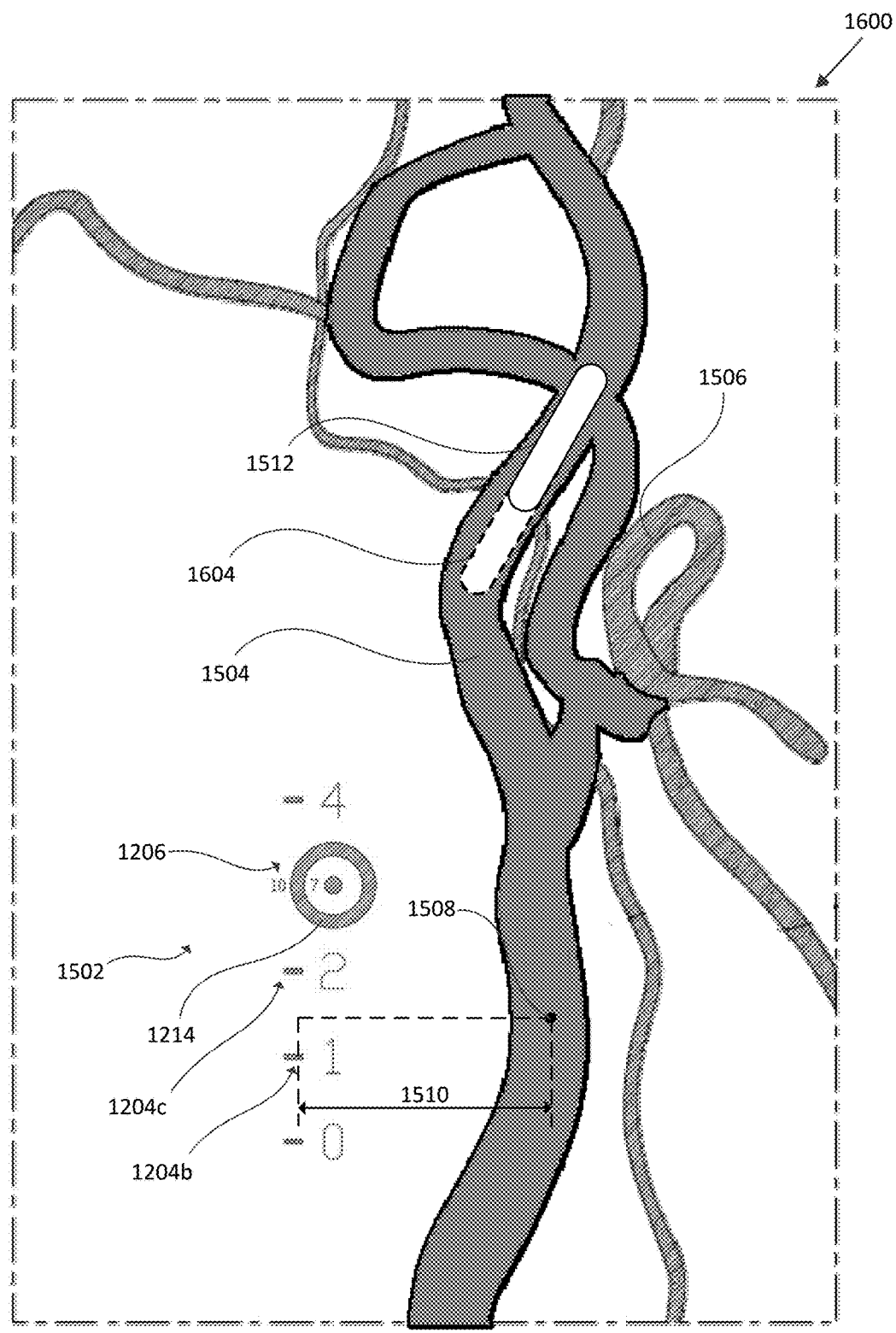
FIG. 16 schematically depicts another implementation of a radiological image that may be produced according to one or more aspects described herein.

FIG. 16 schematically depicts another implementation of a radiological image 1600 that may be produced according to one or more aspects described herein. In one example, the radiological image 1600 may be similar to radiological image 1500. However, in one example, one or more processes may be executed by computer 802 to identify a portion of the synthetic structure 1512 that is radiopaque and visible within the radiological image 1600. Further, one or more processes may be executed to identify the model type of the synthetic structure 1512, and overlay a computer-generated image that indicates a size of an additional portion of the synthetic structure 1512 that is not radiopaque. As such, element 1604 may represent a portion of the synthetic structure 1512 that extends beyond the radiopaque portion visible within a radiological image without a computer-generated overlay. As such, a user may utilize these one or more processes to display a true size of a synthetic structure as it is being delivered into, for example, a blood vessel 1504 of a patient.

Figure 17:
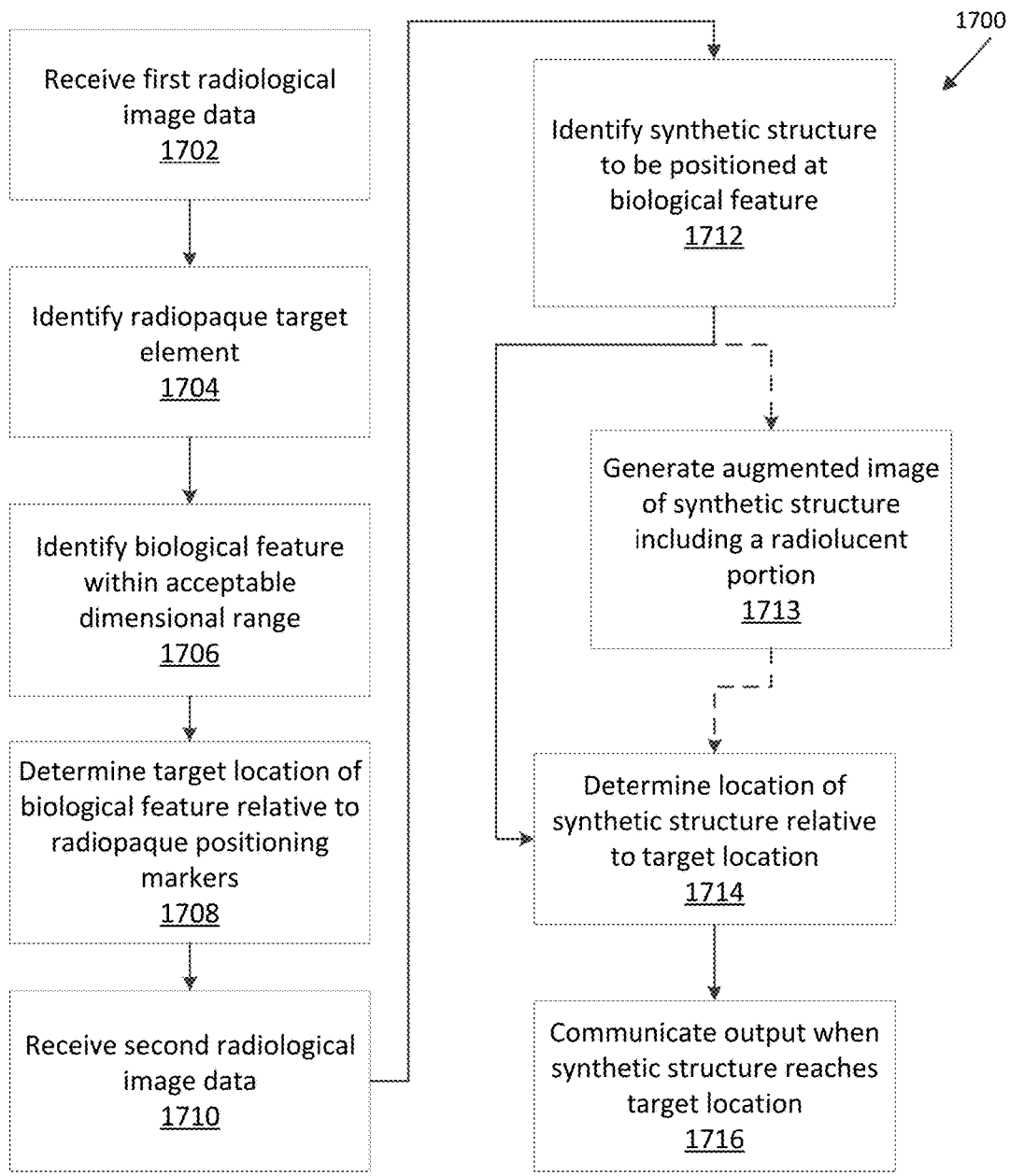
FIG. 17 is a flowchart diagram of a process for identification of a suitable site within a biological feature of a patient for positioning of a synthetic structure, according to one or more aspects described herein.

FIG. 17 is a flowchart diagram of a process for identification of a suitable site within a biological feature of a patient for positioning of a synthetic structure, according to one or more aspects described herein. In one example, flowchart 1700 may be executed using the imaging system 800 from FIG. 8, and one or more of the sizing devices 1200, 1300 and/or 1400 from FIGS. 12, 13, and 14, respectively.

In one implementation, first radiological image data of an area of a body of a patient may be received. This first radiological image data may be generated during a time period when a radiopaque contrast agent is present in one or more biological features within the imaged area. These biological features may include, among others, tissues, organs, blood vessels, blood clots, and the like. In one embodiment, the radiological image data includes at least one vessel having a contrast agent present within at least a portion of a first vessel of the at least one vessel. The radiological image data may be received, from the detector 816, at the processor 804 of computer device 802. These one or more processes to receive the first radiological image data may be executed at block 1702 of flowchart 1700.

In one example, a radiopaque target element may be identified from the received first radiological image data. The target element may be generated by a sizing device, such as one or more of the sizing devices 1200, 1300 and/or 1400 as electromagnetic radiation (e.g. x-rays) is passed through both the imaged area of the body of the patient, and the sizing device positioned on an area of skin of the patient. In one implementation, the radiopaque target element may be identified using one or more image recognition processes executed by the processor 804. Further, the radiopaque target element may be identified at block 1704 of flowchart 1700.

The radiological image data may include images of one or more biological features within the imaged area of the patient's body. The identified radiopaque target element may be utilized to identify a specific location, portion, or entire feature itself that, as dictated by the captured radiologic data, has a dimensional property within an acceptable dimensional range. In one example, the biological feature may be a blood vessel, and the dimensional property may be a diameter of the blood vessel. Further, the target element may indicate a minimum and a maximum vessel diameter for a specific application (which may be mandatory, recommended, considered acceptable, and/or other criteria). In accordance with one aspect, the selected blood vessel (or location or portion thereof) may be identified to have a vessel diameter within the acceptable range between the minimum and maximum acceptable vessel diameters based upon a comparison with the target element as captured by the imaging data.

Accordingly, one or more processes may be executed to identify, from the radiopaque target element, the acceptable dimensional range, and compare it to one or more biological features within the first radiological image data. Further, the one or more processes may identify one or more portions of a biological feature (e.g. one or more sections of a blood vessel of a patient) within the acceptable dimensional range indicated by the radiopaque target element. It is contemplated that additional or alternative criteria may be utilized to identify the biological feature, or a portion thereof. These additional or alternative criteria may include, among others, a length and/or a straightness of the biological feature. It is further contemplated that the radiopaque target element may be compared to the one or more biological features to manually identify a biological feature with a dimensional property within an acceptable dimensional range. Accordingly, one or more manual tools may be utilized. For example, a calipers may be utilized to mark a vessel diameter within the acceptable dimensional range, and compare this marked vessel diameter to one or more portions of blood vessels imaged within the first radiological image data. One or more processes to identify the biological feature, from one or more biological features within the received first radiological image data, may be executed at block 1706 of flowchart 1700.

A target location of the identified biological feature may be determined relative to one or more radiopaque positioning markers of a sizing device, such as one or more of the sizing devices 1200, 1300 and/or 1400, as previously described. In one example, an x- and y-coordinate of a target location of the identified biological feature may be determined. It is contemplated, however, that additional or alternative coordinate systems may be utilized, without departing from the scope of these disclosures. In one example, the target location of the identified biological feature may be calculated by a processor, such as connected to computer 802, and may be communicated to a user as a computer-generated graphical overlay on a radiological image output from, in one example, the user interface 820. In another example, the target location of the identified biological feature may be manually identified by noting a position of the target location relative to one or more of the positioning markers of the sizing device (in addition to the target element serving as a guide for which location of one or more features (or portions thereof) are suitable for receiving the medical device and/or selecting a specific medical device, model of device, or medical device with specific dimensional properties (e.g., diameter). This manual identification may utilize one or more manual tools (e.g. a calipers may be utilized to determine the position of the target location relative to one or more of the radiopaque positioning markers. These one or more processes may be executed at block 1708 of flowchart 1700.

Second radiological image data may be received, such as by the processor 804. The second radiological image data may correspond to the same area of the body of the patient as the first radiological image data. However, the second radiological image data may be captured during a time period when the contrast agent is not present within one or more biological features within the imaged area. As such, in one example, the generated radiological image may not include one or more blood vessels previously visible within the first radiological image described in relation to block 1702. In one implementation, one or more processes may be executed to receive the second radiological image data at block 1710 of flowchart 1700. In this regard, aspects of this disclosure relate to using reduced contrast agent quantities when compared to prior art systems and methods.

A synthetic structure, or a radiopaque portion thereof, may be identified within the received second radiological image data. Accordingly, one or more image recognition processes may be executed to identify the synthetic structure within the second radiological image data. In another example, a user may manually identify the synthetic structure within a second radiological image communicated to the user by the user interface 820. The synthetic structure may comprise, among others, a MEMS device, or a stent, and may be configured to be positioned within the biological feature at the identified target location. One or more processes to identify the synthetic structure to be positioned at the target location of the identified biological feature may be executed at block 1712 of flowchart 1700.

Optionally, one or more processes may be executed to generate an augmented image of the identified synthetic structure. The augmented image may comprise a computer-generated graphical overlay on top of a radiological image that is communicated to the user through the user interface 820. As such, one or more image recognition processes may be utilized to identify a visible portion of the synthetic structure within radiological image data. This visible portion may correspond to a radiopaque portion of the synthetic structure. Further, upon identification of the radiopaque portion of the synthetic structure, a stored description of the synthetic structure may be utilized to identify and generate the graphical overlay that represents at least a portion of the synthetic structure that is radiolucent/radio translucent, and not readily visible within radiological image data. As such, these one or more processes may be executed to generate an augmented image of the synthetic structure that includes a radiolucent portion at block 1713 of flowchart 1700.

A location of the identified synthetic structure relative to the target location may be determined. As such, a user may utilize this information to move the synthetic structure to the target location without, or with reduced, contrast agent being introduced into one or more biological features of a patient. One or more processes to determine the location of the synthetic structure relative to the target location may be executed at block 1714 of flowchart 1700.

An output may be communicated to a user when the synthetic structure is within a threshold distance of the target location. It is contemplated that the output may comprise a visual, an audible, or a haptic feedback signal that is communicated to the user through the user interface 820. It is further contemplated that the threshold distance may include any distance value, without departing from the scope of these disclosures. Accordingly, one or more processes to communicate the output to the user when the synthetic structure is within the threshold distance may be executed at block 1716 of flowchart 1700.

The various embodiments described herein may be implemented by general-purpose or specialized computer hardware. In one example, the computer hardware may comprise one or more processors, otherwise referred to as microprocessors, having one or more processing cores configured to allow for parallel processing/execution of instructions. As such, the various disclosures described herein may be implemented as software coding, wherein those of skill in the computer arts will recognize various coding languages that may be employed with the disclosures described herein. Additionally, the disclosures described herein may be utilized in the implementation of application-specific integrated circuits (ASICs), or in the implementation of various electronic components comprising conventional electronic circuits (otherwise referred to as off-the-shelf components). Furthermore, those of ordinary skill in the art will understand that the various descriptions included in this disclosure may be implemented as data signals communicated using a variety of different technologies and processes. For example, the descriptions of the various disclosures described herein may be understood as comprising one or more streams of data signals, data instructions, or requests, and physically communicated as bits or symbols represented by differing voltage levels, currents, electromagnetic waves, magnetic fields, optical fields, or combinations thereof.

One or more of the disclosures described herein may comprise a computer program product having computer-readable medium/media with instructions stored thereon/therein that, when executed by a processor, are configured to perform one or more methods, techniques, systems, or embodiments described herein. As such, the instructions stored on the computer-readable media may comprise actions to be executed for performing various steps of the methods, techniques, systems, or embodiments described herein. Furthermore, the computer-readable medium/media may comprise a storage medium with instructions configured to be processed by a computing device, and specifically a processor associated with a computing device. As such the computer-readable medium may include a form of persistent or volatile memory such as a hard disk drive (HDD), a solid state drive (SSD), an optical disk (CD-ROMs, DVDs), tape drives, floppy disk, ROM, RAM, EPROM, EEPROM, DRAM, VRAM, flash memory, RAID devices, remote data storage (cloud storage, and the like), or any other media type or storage device suitable for storing data thereon/therein. Additionally, combinations of different storage media types may be implemented into a hybrid storage device. In one implementation, a first storage medium may be prioritized over a second storage medium, such that different workloads may be implemented by storage media of different priorities.

Further, the computer-readable media may store software code/instructions configured to control one or more of a general-purpose, or a specialized computer. Said software may be utilized to facilitate interface between a human user and a computing device, and wherein said software may include device drivers, operating systems, and applications. As such, the computer-readable media may store software code/instructions configured to perform one or more implementations described herein.

Those of ordinary skill in the art will understand that the various illustrative logical blocks, modules, circuits, techniques, or method steps of those implementations described herein may be implemented as electronic hardware devices, computer software, or combinations thereof. As such, various illustrative modules/components have been described throughout this disclosure in terms of general functionality, wherein one of ordinary skill in the art will understand that the described disclosures may be implemented as hardware, software, or combinations of both.

The one or more implementations described throughout this disclosure may utilize logical blocks, modules, and circuits that may be implemented or performed with a general-purpose processor, a digital signal processor (DSP), an application-specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, or any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The techniques or steps of a method described in connection with the embodiments disclosed herein may be embodied directly in hardware, in software executed by a processor, or in a combination of the two. In some embodiments, any software module, software layer, or thread described herein may comprise an engine comprising firmware or software and hardware configured to perform embodiments described herein. Functions of a software module or software layer described herein may be embodied directly in hardware, or embodied as software executed by a processor, or embodied as a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read data from, and write data to, the storage medium. In the alternative, the storage medium may be integral to the processor. The processor and the storage medium may reside in an ASIC. The ASIC may reside in a user device. In the alternative, the processor and the storage medium may reside as discrete components in a user device.

Accordingly, it will be understood that the disclosure is not to be limited to the embodiments disclosed herein, but is to be understood from the following claims, which are to be interpreted as broadly as allowed under the law.

I claim:

1. A non-transitory computer-readable medium comprising computer-executable instructions, that when executed, cause a processor to:
   receive first radiological image data of an area of a body of a patient as a radiopaque contrast agent is present in one or more biological features within the area;
   identify, from the received first radiological image data, a radiopaque target element of a sizing device positioned on an area of skin of the patient;
   compare the radiopaque target element to the one or more biological features to identify a biological feature, from the one or more biological features, with a dimensional property within an acceptable dimensional range indicated by the radiopaque target element;
   determine a target location of the biological feature relative to one or more radiopaque positioning markers of the sizing device;
   receive second radiological image data of the area of the body of the patient;
   identify, from the second radiological image data, a radiopaque portion of a synthetic structure to be positioned at the biological feature; and
   determine a location of the radiopaque portion of the synthetic structure relative to the target location.

2. The non-transitory computer-readable medium of claim 1, wherein the biological feature is not visible in the second radiological image data.

3. The non-transitory computer-readable medium of claim 1, wherein the computer-executable instructions, when executed, further cause the processor to:
    identify one or more one or more radiopaque symbols corresponding to the one or more radiopaque positioning markers.

4. The non-transitory computer-readable medium of claim 1, wherein the computer-executable instructions, when executed, further cause the processor to:
    generate, based on the identified radiopaque portion of the synthetic structure, an augmented image of the synthetic structure that includes the radiopaque portion and a radiolucent portion of the synthetic structure.

5. The non-transitory computer-readable medium of claim 1, wherein the synthetic structure comprises a MEMS device.

6. The non-transitory computer-readable medium of claim 1, wherein the biological feature is a portion of a blood vessel of the patient.

7. The non-transitory computer-readable medium of claim 6, wherein the dimensional property is a width of the blood vessel.

8. A method comprising:
    receiving first radiological image data of an area of a body of a patient as a radiopaque contrast agent is present in one or more biological features within the area;
    identifying, from the received first radiological image data, a radiopaque target element of a sizing device positioned on an area of skin of the patient;
    comparing the radiopaque target element to the one or more biological features to identify a biological feature, from the one or more biological features, with a dimensional property within an acceptable dimensional range indicated by the radiopaque target element;
    determining a target location of the biological feature relative to one or more radiopaque positioning markers of the sizing device;
    receiving second radiological image data of the area of the body of the patient;
    identifying, from the second radiological image data, a radiopaque portion of a synthetic structure to be positioned at the biological feature; and
    determining a location of the radiopaque portion of the synthetic structure relative to the target location.

9. The method of claim 8, wherein the biological feature is not visible in the second radiological image data.

10. The method of claim 8, further comprising:
    identifying one or more radiopaque symbols corresponding to the one or more radiopaque positioning markers.

11. The method of claim 8, wherein the sizing device further comprises a radiopaque marking indicating a total size of the synthetic structure that includes the radiopaque portion and a radiolucent portion of the synthetic structure.

12. The method of claim 8, wherein the synthetic structure comprises a MEMS device.

13. The method of claim 8, wherein the biological feature is a portion of a blood vessel of the patient.

14. The method of claim 13, wherein the dimensional property is a width of the blood vessel.

15. The method of claim 8, wherein the radiopaque target element comprises a ring with two diameters indicating a minimum and a maximum acceptable dimension within the acceptable dimensional range.

16. A sizing device, comprising:
    a planar base structure having a front surface and a back surface, wherein the base structure is:
        configured to be placed on a user's skin during radiological imaging of a target area of the user; and
        radiolucent to light with a wavelength in the visible spectrum;
    a series of radiopaque positioning markers positioned on the base structure and spaced apart along a longitudinal axis of the sizing device;
    a radiopaque target element positioned on the front surface of the base structure, wherein the radiopaque target element indicates an acceptable dimensional range of a biological feature for positioning of a synthetic structure therein; and
    an adhesive layer on the back surface of the device configured to adhere the device to the user's skin.

17. The sizing device of claim 16, wherein the radiopaque target element comprises a radiopaque ring.

18. The sizing device of claim 17, wherein the radiopaque target is centered at a radiopaque positioning marker, between a first positioning marker and a last positioning marker, from the series of radiopaque positioning markers.

19. The sizing device of claim 18, wherein a distance between a center of the radiopaque target element and the first positioning marker indicates a length of the synthetic structure.

20. The sizing device of claim 16, wherein the synthetic structure is a MEMS device configured to be positioned within a blood vessel of the user.

* * * * *